United States Patent
Idelevich et al.

(10) Patent No.: US 9,709,556 B2
(45) Date of Patent: *Jul. 18, 2017

(54) DEVICES AND METHODS FOR DETERMINING AND/OR ISOLATING CIRCULATING CANCER CELLS

(71) Applicant: Analiza, Inc., Bay Village, OH (US)

(72) Inventors: Pavel Idelevich, Hingham, MA (US); Arnon Chait, Bay Village, OH (US); Alan Bauer, Jerusalem (IL)

(73) Assignee: Analiza, Inc., Bay Village, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/225,512

(22) Filed: Mar. 26, 2014

(65) Prior Publication Data
US 2015/0160196 A1    Jun. 11, 2015

Related U.S. Application Data

(63) Continuation-in-part of application No. 14/103,170, filed on Dec. 11, 2013, now abandoned.

(51) Int. Cl.
G01N 33/50    (2006.01)
G01N 33/574    (2006.01)

(52) U.S. Cl.
CPC ..... G01N 33/5094 (2013.01); G01N 33/5005 (2013.01); G01N 33/5091 (2013.01); G01N 33/57492 (2013.01); G01N 2333/70514 (2013.01); G01N 2333/70517 (2013.01)

(58) Field of Classification Search
CPC ........... G01N 33/5005; G01N 33/5091; G01N 33/5094
See application file for complete search history.

(56) References Cited

U.S. PATENT DOCUMENTS

| | | | |
|---|---|---|---|
| 5,547,849 | A | 8/1996 | Baer et al. |
| 6,793,642 | B2 | 9/2004 | Connelly et al. |
| 7,507,395 | B2 | 3/2009 | Diwu et al. |
| 7,855,078 | B2 | 12/2010 | Evans |
| 8,062,609 | B2 | 11/2011 | Krager et al. |
| 8,097,404 | B2 | 1/2012 | Ribault et al. |
| 8,548,219 | B2 | 10/2013 | Ortyn et al. |
| 8,551,425 | B2 | 10/2013 | Goldkorn et al. |
| 8,834,794 | B2 | 9/2014 | Yazdanpanah et al. |
| 9,063,127 | B1 | 6/2015 | Idelevich et al. |
| 9,250,242 | B2 | 2/2016 | Martin et al. |
| 2003/0119206 | A1 | 6/2003 | Shai |
| 2005/0287547 | A1 | 12/2005 | Seligman |
| 2007/0015171 | A1 | 1/2007 | Bianchi |
| 2009/0061456 | A1 | 3/2009 | Allard et al. |
| 2011/0195413 | A1 | 8/2011 | Lin |
| 2013/0078667 | A1 | 3/2013 | Goodman et al. |
| 2013/0102021 | A1 | 4/2013 | Beacham et al. |
| 2013/0130226 | A1 | 5/2013 | Lim et al. |
| 2013/0266960 | A1 | 10/2013 | Idelevich et al. |
| 2014/0106388 | A1 | 4/2014 | Bangert et al. |
| 2014/0133733 | A1 | 5/2014 | Grady et al. |
| 2015/0160198 | A1 | 6/2015 | Idelevich et al. |
| 2015/0160246 | A1 | 6/2015 | Idelevich et al. |

FOREIGN PATENT DOCUMENTS

| | | |
|---|---|---|
| CA | 2 654 782 | 1/2008 |
| CN | 101438143 | 5/2009 |
| CN | 103866016 A | 6/2014 |
| EP | 0 057 809 A2 | 1/1982 |
| EP | 0 221 768 A2 | 10/1986 |
| EP | 0 499 693 A2 | 11/1991 |
| EP | 0 582 836 A1 | 7/1993 |
| EP | 2 064 290 | 9/2004 |
| EP | 1 984 030 | 8/2007 |
| EP | 1 597 353 | 8/2013 |
| WO | WO 92/02632 A1 | 2/1992 |
| WO | WO 94/02646 A1 | 2/1994 |
| WO | WO 96/34604 A1 | 11/1996 |

(Continued)

OTHER PUBLICATIONS

Gambino et al. "Acidification of Blood is Superior to Sodium Fluoride Alone as an Inhibitor of Glycolysis" (2009) Clincial Chemistry, vol. 55, No. 5: 1019-1021.*
Gulley et al. "Genetic Tests to Evaluate Prognosis and Predict Therapeutic Response in Acute Myeloid Leukemia" (2010) Journal of Molecular Diagnostics, vol. 12, No. 1: 3-16.*
Han and Burgess "Fluorescent Indicators for Intracelluar pH" (2010) Chemical Review, vol. 110: 2709-2728.*
Harguindey et al. "The role of pH dynamics and the Na/H antiporter in the etiopathogenesis and treatment of cancer. Two faces of the same coin—one single nature." (2005), Biochemi et Biophysica Acta, vol. 1756: 1-24.*

(Continued)

Primary Examiner — Teresa E Knight
(74) Attorney, Agent, or Firm — Wolf, Greenfield & Sacks, P.C.

(57) ABSTRACT

The present invention generally relates to devices and methods for determining and/or isolating cells. One aspect is generally directed to methods and devices for detecting, identifying, counting, and/or potentially sorting cells of interest in blood or other biological sample. In some embodiments, blood samples (or other biological fluids) may be treated with signaling entities, such as pH-sensitive entities, that change color or otherwise produce a signal in suitable internal environments. For example, certain cells, such as cancer or fetal cells, may have differences in intracellular pH compared to other cells, which can be detected using pH-sensitive entities. In certain embodiments, the cells may be sorted based on such signaling entities; for example, illumination of cells in a suitable machine for sorting cells (e.g., using fluorescent light) may allow determination of the cells, which may also be recovered or isolated for further manipulation in some cases.

15 Claims, 17 Drawing Sheets

(56) References Cited

FOREIGN PATENT DOCUMENTS

| | | |
|---|---|---|
| WO | WO 00/75237 A3 | 12/2000 |
| WO | WO 02/40703 A1 | 5/2002 |
| WO | WO 2004/076643 A2 | 9/2004 |
| WO | WO 2005/080944 A1 | 9/2005 |
| WO | WO 2006/097051 A1 | 9/2006 |
| WO | WO 2007/065438 A2 | 6/2007 |
| WO | WO 2007/089911 A2 | 8/2007 |
| WO | WO 2008/057437 A2 | 5/2008 |
| WO | WO 2008/076524 A2 | 6/2008 |
| WO | WO 2008/117195 A2 | 10/2008 |
| WO | WO 2008/132755 A1 | 11/2008 |
| WO | WO 2010/078872 A2 | 7/2010 |
| WO | WO 2011/025976 A2 | 3/2011 |
| WO | WO 2013/075100 A1 | 5/2013 |
| WO | WO 2013/119924 A1 | 8/2013 |
| WO | WO 2013/147114 A1 | 10/2013 |
| WO | WO 2013/152059 A1 * | 10/2013 ............ A61K 47/48 |
| WO | WO 2014/138183 A1 | 9/2014 |
| WO | WO 2015/112999 A1 | 7/2015 |

OTHER PUBLICATIONS

Murphy and Garder "Platelet Storage at 22 C: Role of Gas Transport Across Plastic Containers in Maintenance of Viability" (1975), Blood, vol. 46, No. 2: 209-218.*

Agarwal et al., "Commercial landscape of noninvasive prenatal testing in the United States,"Prenatal Diagnosis, 2013 (May 17, 2013), 33:521-531.

Obokata et al., "Bidirectional development potential in reprogrammed cells with acquired pluripotency," Nature, Jan. 30, 2014 505:676-687.

Obokata et al., "Stimulus-triggered fate conversion of somatic cells into pluripotency," Nature, Jan. 30, 2014 505:641-658.

Ozkan et al., "A rapid method for measuring interacellular pH using BCECF-AM," 2002 (date and month unknown), BBA, 2002 (Aug. 15, 2002), 1572:143-148.

Plaks et al., "Circulating tumor cells," Science, (Sep. 13, 2013), 341:1186-1188 [downloaded from www.sciencemag.org on Sep. 25, 2013].

Reiseberg et al., "Flow cytometry in biotechnology," Appl. Microbiol. Biotechnol, Jun. 23, 2001 56:350-360.

Invitation to Pay Additional Fees from International Application No. PCT/US2014/069340 mailed Feb. 23, 2015.

International Search Report and Written Opinion from International Application No. PCT/US2014/069340 mailed Apr. 23, 2015.

Nagavarapu, Circulating Tumor Cell (CTC) Diagnostics: Technologies and Global Markets. BCC Research. Jan. 2014. Chapters 5-7. 75-166.

Sitar et al., The use of non-physiological conditions to isolate fetal cells from maternal blood. Experimental Cell Research. Jan. 15, 2005. 302(2):153-161.

Van Erp et al., Ratiometric measurement of intracellular pH in cultured human keratinocytes using carboxy-SNARF-1 and flow cytometry. Cytometry. 1991;12(2):127-32.

Alix-Panabières et al., Challenges in circulating tumour cell research. Nat Rev Cancer. Sep. 14, 2014(9):623-31. doi: 10.1038/nrc3820. Epub Jul. 31, 2014.

Costa et al., Biosensors for the detection of circulating tumour cells. Sensors (Basel). Mar. 10, 2014;14(3):4856-75. doi:10.3390/s140304856.

Deng et al., Single cell mutational analysis of PIK3CA in circulating tumor cells and metastases in breast cancer reveals heterogeneity, discordance, and mutation persistence in cultured disseminated tumor cells from bone marrow. BMC Cancer. Jun. 19, 2014;14:456. doi: 10.1186/1471-2407-14-456.

Ferreira et al., Circulating tumor cell technologies. Mol Oncol. Mar. 2016;10(3):374-94. doi: 10.1016/j.molonc.2016.01.007. Epub Jan. 28, 2016.

Gabriel et al., Circulating Tumor Cells: A Review of Non-EpCAM-Based Approaches for Cell Enrichment and Isolation. Clin Chem. Apr. 2016;62(4):571-81. doi: 10.1373/clinchem.2015.249706. Epub Feb. 19, 2016.

Gao et al., Decreased intracellular pH induced by cariporide differentially contributes to human umbilical cord-derived mesenchymal stem cells differentiation. Cell Physiol Biochem. 2014;33(1):185-94. doi: 10.1159/000356661. Epub Jan. 24, 2014.

Giuliano et al., Circulating and disseminated tumor cells from breast cancer patient-derived xenograft-bearing mice as a novel model to study metastasis. Breast Cancer Res. Jan. 9, 2015;17:3. doi: 10.1186/s13058-014-0508-5.

Haber et al., Blood-based analyses of cancer: circulating tumor cells and circulating tumor DNA. Cancer Discov. Jun. 2014;4(6):650-61. doi:10.1158/2159-8290.CD-13-1014. Epub May 6, 2014.

Harouaka et al., Circulating tumor cell enrichment based on physical properties. J Lab Autom. Dec. 2013;18(6):455-68. doi:10.1177/2211068213494391. Epub Jul. 5, 2013.

Hartkopf et al., Simultaneous Detection of Disseminated and Circulating Tumor Cells in Primary Breast Cancer Patients. Cancer Res Treat. Jan. 2016;48(1):115-24. doi: 10.4143/crt.2014.287. Epub Feb. 16, 2015.

Joosse et al., Biology, detection, and clinical implications of circulating tumor cells. EMBO Mol Med. Nov. 14, 2014;7(1):1-11. doi:10.15252/emmm.201303698.

Li et al., Mesenchymal stem cells are injured by complement after their contact with serum. Blood. Oct. 25, 2012;120(17):3436-43. doi:10.1182/blood-2012-03-420612. Epub Sep. 10, 2012.

Yap et al., Circulating tumor cells: a multifunctional biomarker. Clin Cancer Res. May 15, 2014;20(10):2553-68. doi:10.1158/1078-0432.CCR-13/2664.

Yu et al., Cancer therapy. Ex vivo culture of circulating breast tumor cells for individualized testing of drug susceptibility. Science. Jul. 11, 2014;345(6193):216-20. doi: 10.1126/science.1253533.

Extended European Search Report for International Application No. EP 1480632.8.

Cohen et al., Determination of intracellular pH and compartmentation using diffusion-weighted NMR spectroscopy with pH-sensitive indicators. Magn Reson Med. May 2004;51(5):900-3.

Garciandia et al., Enhanced Na(+)-H+ exchanger activity and NHE-1 mRNA expression in lymphocytes from patients with essential hypertension. Hypertension. Mar. 1995;25(3):356-64.

Webb et a., Dysregulated pH: a perfect storm for cancer progression. Nat Rev Cancer. Aug. 11, 2011;11(9):671-7. doi: 10.1038/nrc3ll0.

International Preliminary Report on Patentability for Application No. PCT/US2014/069340 mailed Jun. 23, 2016.

* cited by examiner

DEVICES AND METHODS FOR DETERMINING AND/OR ISOLATING CIRCULATING CANCER CELLS

RELATED APPLICATIONS

This application is a continuation-in-part of U.S. patent application Ser. No. 14/103,170, filed Dec. 11, 2013, entitled "Devices and Methods for Determining and/or Isolating Cells Such as Circulating Cancer or Fetal Cells," incorporated herein by reference in its entirety.

FIELD

The present invention generally relates to devices and methods for determining and/or isolating cells.

BACKGROUND

There are many systems where the isolation of specific cells from a larger number or population of cells is highly desirable. For example, circulating tumor cells (CTC's) are cancer cells that have been displaced from their associated tumors and may enter the blood system or other parts of the vasculature. CTC's may offer information with respect to the condition and progress of a cancer; they may also serve to cause cancerous growths at other points within a body, e.g., at locations where there was no cancerous legion prior to the arrival and plastic growth of the CTC's. Circulating fetal cells (CFC's) are similar to CTC's in that they are often found in very low concentration in the blood; their obvious source is from a developing fetus in the mother's womb. CFC's may offer a rich potential for genetic analysis of a fetus at very early stages of fetal development.

Because of the importance of CTC's and CFC's, their determination and/or isolation and use in genetic and medical analyses is extremely valuable. The major challenge with these cell groups is their low circulating numbers: there may be a few tens of such cells per milliliter of blood, as opposed to the millions of white blood cells and the like, and many millions of red blood cells.

SUMMARY

The present invention generally relates to devices and methods for determining and/or isolating cells. The subject matter of the present invention involves, in some cases, interrelated products, alternative solutions to a particular problem, and/or a plurality of different uses of one or more systems and/or articles.

In one aspect, the invention is generally directed to methods and devices for rapidly identifying and isolating predetermined cell species within a biological fluid containing a large number of non-target cells.

In some embodiments, the invention includes a device for the detection and optionally sorting of circulating tumor or fetal cells, including: a biological fluid containing a plurality of cells; a pH-sensitive dye or other signaling molecule adapted to be internalized by at least some of the plurality of cells; and a machine capable of detecting and optionally sorting cells in response to a signal corresponding to predetermined pH within the cells.

In one aspect of the device, the machine capable of detecting said signal and optionally counting cells is a cell cytometer.

In another aspect of the device, the machine capable of detecting said signal and optionally sorting cells is a cell sorter.

In one aspect of the device, the circulating tumor cells are associated with at least one of the following cancers: lymphomas, sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, synovioma, mesothelioma, lymphangioendotheliosarcoma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, non-small cell lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia and heavy chain.

In another aspect of the device, the pH-sensitive dye is adapted to give a predetermined color at basic pH values.

In another aspect of the device, the detection step is followed by a cell sorting step.

In another aspect of the device, the cell sorting machine is adapted to include a source of electromagnetic radiation.

In another aspect of the device, the cell sorting machine is a fluorescent microscope.

In another aspect of the device, the cell sorting machine is a fluorescent microscope with automated slide screening to identify and optionally isolate cells.

In another aspect of the device, the electromagnetic radiation is selected from white light, laser light at a predetermined at least one wavelength, visible light at at least one predetermined wavelength, fluorescent light, x-ray radiation, or microwave radiation or a combination of different forms of electromagnetic radiation.

In another aspect of the device, the cell sorting machine is adapted to communicate results to a computing device.

In another aspect of the device, the computing device is realized as a mobile computing device, smartphone, cellular phone, tablet computer, laptop computer or tabletop computer.

In another aspect of the device, the pH-sensitive dye is selected from the following: 2',7'-bis(2-carboxyethyl)-5(6)-carboxyfluorescein tetrakis(acetoxymethyl) ester (BCECF AM), 5(6)-carboxy-2',7'-dichlorofluorescein, 5(6)-carboxyfluorescein, 5(6)-carboxyfluorescein diacetate, 5(6)-carboxyfluorescein N-hydroxysuccinimide ester, 3,6-diacetoxyphthalonitrile, 6,8-dihydroxy-1,3-pyrenedisulfonic acid disodium salt, Eosin diacetate, or naphthofluorescein.

In another aspect of the device, the pH-sensitive dye is realized as a plurality of pH-sensitive dyes.

In another aspect of the device, one of more dyes that are conjugated to antibodies targeting specific cell antigens are also included.

In another aspect of the device, the cell cytometer or sorter identifies and optionally sorts circulating cells in conjunction with a response from the pH-sensitive dye and at least one additional dye that is conjugated to an antibody targeting a specific cell antigen.

In certain embodiments, the invention includes a device comprising a fluid comprising target cells of interest and non-target cells, a pH-sensitive entity internalized within the cells, and a cell cytometer containing the fluid. In some cases, the pH-sensitive entity has a first state within the target cells of interest and a second state within the non-target cells.

In another aspect, the invention includes a device comprising a fluid comprising cells, a pH-sensitive entity contained within at least some of the cells, and a cell cytometer containing the fluid.

In another aspect, the invention includes a device for identifying a cell type. In some cases, the device includes a fluid comprising target cells and non-target cells, a pH-sensitive that is fluorescent at a pH equal to the intracellular pH of the target cells and is substantially less fluorescent at a pH equal to the intracellular pH of the non-target cells, and optionally, a cell cytometer containing the fluid. In some cases, said target cells have an intracellular pH higher than an intracellular pH of said non-target cells.

In another aspect, the present invention is generally directed to a device, e.g., a device for determining and/or isolating cells such as cancer cells or fetal cells. In one set of embodiments, for instance, the device comprises a fluid comprising cells, a pH-sensitive entity internalized within at least some of the cells, and a cell cytometer containing the fluid.

The invention includes, in another set of embodiments, a method for specifically detecting, and optionally isolating circulating tumor cells including: providing a predetermined volume of a biological fluid, the fluid containing a plurality of cells; adding to the fluid a predetermined amount of a pH-sensitive dye adapted to give a predetermined response when exposed to a given form of electromagnetic radiation when the dye is present in an environment of a known pH range; allowing the plurality of cells in the fluid and the dye to incubate for a predetermined period of time to allow said dye to be internalized within the cells; placing a portion of the biological fluid in a machine capable of detecting and optionally sorting the cells based on detection of said predetermined response corresponding to a specific pH within the cells.

In one aspect of the method, the step of detection and optionally sorting is conducted with a laser using a cell cytometer or optionally a cell sorter.

In another aspect of the method, the number of cells detected per unit volume of the biological fluid is used to determine the stage of cancer, In yet another aspect of the method, the number of cells detected per unit volume of the biological fluid is used for early detection of cancer, or for monitoring disease progression, or for monitoring response to treatment, or to detect disease recurrence.

In one aspect of the method, there is an additional step of performing genetic, morphology or cytopathology analysis of the circulating tumor cells.

In another aspect of the method, there is an additional step of identifying at least one form of cancer associated with the circulating tumor cells.

In another aspect of the method, the count of the circulating tumor cells detected by the cell cytometer machine is used to assess a clinical condition.

In another aspect of the method, the predetermined period of time is between 1 minute and two hours.

In another aspect of the method, the biological fluid is selected from blood, blood serum, cerebral spinal fluid, urine, nipple aspirate, saliva, phlegm, pleural or abdominal exudate or transudate.

In another aspect of the method, there is an additional step of incubating the biological fluid with a buffer a predetermined pH prior to the step of adding.

In another aspect of the method, a plurality of incubations of the biological fluid are performed with a plurality of buffers, each with a different pH.

In another aspect of the method, the cells are selected for further analysis from the groups of isolated cells corresponding to the plurality of buffers.

In another aspect of the method, the electromagnetic radiation is selected from white light, laser light at a predetermined at least one wavelength, visible light at at least one predetermined wavelength, fluorescent light, x-ray radiation, microwave radiation or a combination of different forms of electromagnetic radiation.

In another aspect of the method, one of more dyes that are conjugated to antibodies or magnetic nanoparticles coated with antibodies targeting specific cell antigens are also included.

In another aspect of the method, the cell sorting step is conducted in response to the pH-sensitive dye and at least one additional dye that is conjugated to an antibody, or a magnetic nanoparticles coated with antibodies, targeting a specific cell antigen.

In another aspect of the method, the at least one additional antibody that is conjugated to the at least one additional dye is specific to detect epithelial-specific markers or tumor-specific antigens present on the CTC surface: EpCAM, EphB4, HER2, EGFR, CEA, MUC-1, negative selection for CD45, or other antigens known in cancer cell biology.

In another aspect of the method, a pre-fractionation step is included to remove predetermined cell fractions before incubating with the pH-sensitive dye.

In another aspect of the method, the pre-fractionation step is designed to remove red blood cells by lysing.

The invention additionally includes, in yet another aspect, a method for specifically isolating circulating fetal cells including: providing a predetermined volume of a biological fluid, the fluid containing a plurality of cells; adding to the fluid a predetermined amount of a pH-sensitive dye adapted to give a predetermined response when exposed to a given form of electromagnetic radiation when the dye is present in an environment of a known pH range; allowing the plurality of cells in the fluid and the dye to incubate for a predetermined period of time to allow said dye to be internalized within the cells; placing a portion of the biological fluid in a machine capable of detecting and optionally sorting the cells based on detection of said predetermined response corresponding to a specific pH within the cells.

In one aspect of the method, the step of detection and optionally sorting is conducted with a laser using a cell cytometer or optionally a cell sorter.

In one aspect of the method, there is an additional step of performing karyotyping or genetic analysis on the circulating fetal cells.

In another aspect of the method, the biological fluid is blood or amniotic fluid.

In another aspect of the method, the isolation of circulating fetal cells from blood could be performed as early as 5 or 6 weeks following gestation.

In another aspect of the method, the circulating fetal cells isolated from maternal blood are associated with the fetus and not from persistent fetal cells that are related to a prior pregnancy.

In another aspect of the method, a pre-fractionation step is included to remove predetermined cell fractions before incubating with the pH-sensitive dye.

In another aspect of the method, the pre-fractionation step is designed to remove red blood cells by lysing.

In another aspect of the method, the pH-sensitive dye is selected from the following:
2',7'-bis(2-carboxyethyl)-5(6)-carboxyfluorescein tetrakis (acetoxymethyl) ester (BCECF AM), 5(6)-carboxy-2',7'-dichlorofluorescein, 5(6)-carboxyfluorescein, 5(6)-carboxyfluorescein diacetate, 5(6)-carboxyfluorescein N-hydroxysuccinimide ester, 3,6-diacetoxyphthalonitrile, 6,8-dihydroxy-1,3-pyrenedisulfonic acid disodium salt, Eosin diacetate, naphthofluorescein.

In another aspect of the method, the genetic analysis includes a search for genetic abnormalities.

In another aspect of the method, the pH-sensitive dye is realized as a plurality of pH-sensitive dyes.

In another aspect of the method, the pH-sensitive dye is adapted to give a predetermined fluorescent radiation at basic pH values.

In another aspect of the method, the cell sorting machine is adapted to include a source of electromagnetic radiation.

In another aspect of the method, the electromagnetic radiation is selected from white light, laser light at a predetermined at least one wavelength, visible light at at least one predetermined wavelength, fluorescent light, x-ray radiation, or microwave radiation or a combination of different forms of electromagnetic radiation.

In another aspect of the method, one of more dyes that are conjugated to antibodies, or magnetic nanoparticles coated with antibodies, targeting specific cell antigens are also included.

In another aspect of the method, the cell sorting step is conducted in response to the pH-sensitive dye and at least one additional dye that is conjugated to an antibody targeting a specific cell antigen.

In another aspect of the method, the antibody is specific to CD4, CD8, CD45, CD71, anti-epsilon globin, and fetal hemoglobin.

In another aspect of the method, further selection of fetal cells at early stage of pregnancy is performed using two additional antibody types, specific to CD4 and CD8, respectively, whereas cells missing both or having both antigens are further selected as fetal cells, and those displaying only one type of antigen CD4 or CD8 are recognized as maternal cells.

In another aspect of the method, the cell sorting machine is adapted to communicate results to a computing device.

In another aspect of the method, the computing device is realized as a mobile computing device, smartphone, cellular phone, tablet computer, laptop computer or tabletop computer.

In another aspect of the method, the cells are selected for further analysis from the groups of isolated cells from a plurality of buffers.

In another aspect of the method, there is an additional step of performing morphological analysis of the circulating fetal cells, after placing of sorted cells on the glass slide and staining by one of the conventional staining, for instance, Giemza stain, H&E stain, etc.

In another aspect, the present invention is generally directed to a method of determining cells of interest within a fluid. In one set of embodiments, the method comprises exposing a fluid containing cells to a pH-sensitive entity, determining the pH-sensitive entity within at least some of the cells within the fluid, and determining cells of interest based on the determination of the pH-sensitive entity within the cells.

In another aspect of the method, there is a step of immunostaining with organ-specific antibodies for investigation of localization of a tumor.

The invention includes, in another aspect, a method of determining target cells of interest within a fluid. In some embodiments, the method includes exposing a fluid containing target cells of interest and non-target cells to a pH-sensitive entity, determining the pH-sensitive entity internally within at least some of the cells within the fluid, and determining the target cells of interest based on the determination of the pH-sensitive entity within the cells. In some cases, the pH-sensitive entity has a first state within the target cells of interest and a second state within the non-target cells.

The invention includes, in another aspect, a method of determining target cells of interest within a fluid. In some embodiments, the method includes exposing a fluid containing target cells of interest and non-target cells to a pH-sensitive entity, determining the pH-sensitive entity internally within at least some of the cells within the fluid, and determining the target cells of interest based on the determination of the pH-sensitive entity within the cells. In some cases, the target cells of interest have an intracellular pH at least about 0.1 pH units higher than an intracellular pH of the non-target cells.

The invention includes, in another aspect, a method of determining cells of interest within a fluid. In some embodiments, the method includes exposing a fluid containing cells to a pH-sensitive entity, determining the pH-sensitive entity internally within at least some of the cells within the fluid, and determining cells of interest based on the determination of the pH-sensitive entity within the cells.

The invention includes, in another aspect, a method of determining cells of interest. In some embodiments, the method includes exposing a fluid containing target cells and non-target cells, wherein an intracellular pH of said target cells is at least about 0.1 pH units higher than an intracellular pH of said non-target cells, to a pH-sensitive entity able to fluoresce at or about said intracellular pH of said at least one target cell, determining said pH-sensitive entity in said at least one target cell, and determining cells of interest based on the determination of the pH-sensitive entity within said at least one target cell.

The invention includes, in another aspect, a method of determining cells of interest within a fluid. In some embodiments, the method includes exposing a fluid containing cells to a non-specific signaling entity, determining the non-specific signaling entity internally within at least some of the cells within the fluid, and determining cells of interest based on the determination of the non-specific signaling entity within the cells.

In another aspect, the present invention encompasses methods of making one or more of the embodiments described herein. In still another aspect, the present invention encompasses methods of using one or more of the embodiments described herein.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

The present invention generally relates to devices and methods for determining and/or isolating cells. One aspect is generally directed to methods and devices for detecting, identifying, counting, and/or potentially sorting cells of interest in blood or other biological sample. In some embodiments, blood samples (or other biological fluids) may be treated with signaling entities, such as pH-sensitive entities, that change color or otherwise produce a signal in suitable internal environments. For example, certain cells, such as cancer or fetal cells, may have differences in intracellular pH compared to other cells, which can be detected using pH-sensitive entities. In certain embodiments, the cells may be sorted based on such signaling entities; for example, illumination of cells in a suitable machine for sorting cells (e.g., using fluorescent light) may allow determination of the cells, which may also be recovered or isolated for further manipulation in some cases.

The present invention, in some embodiments thereof, relates to systems and devices for determining cells that may represent a very small proportion of cells in a fluid such as blood, in some cases quickly and facilely. Examples of such cells include, but are not limited to, circulating tumor or fetal cells. The present invention, in some embodiments, provides for isolation of such cells, e.g., for potential genetic or other investigation. Certain embodiments of the present invention could be employed for a wide variety of applications including, but not limited to, cancer screening, genetic testing, individualized medicine to include customization of therapy based on genetic or other features found in cells such as tumor cells, assessment of metastatic potential, recurrence monitoring, or other purposes. Other examples include, but are not limited to, pre-natal screening, genetic testing to assess potential medical conditions, or other purposes.

Some embodiments of the invention are generally directed to the determination of cells, such as tumor cells or fetal cells, within a larger number or population of cells. In some cases, less than about 1% of the population of cells may be the cells which are desired to be determined and/or isolated; in other cases, this may be less than about 0.1%, less than about 0.01%, less than about 0.001%, less than about $10^{-4}$%, less than about $10^{-5}$%, or less than about $10^{-6}$%. The cells may be suspended in blood, or another fluid (e.g., saline, cell media, amniotic fluid, etc.).

Figure 1:
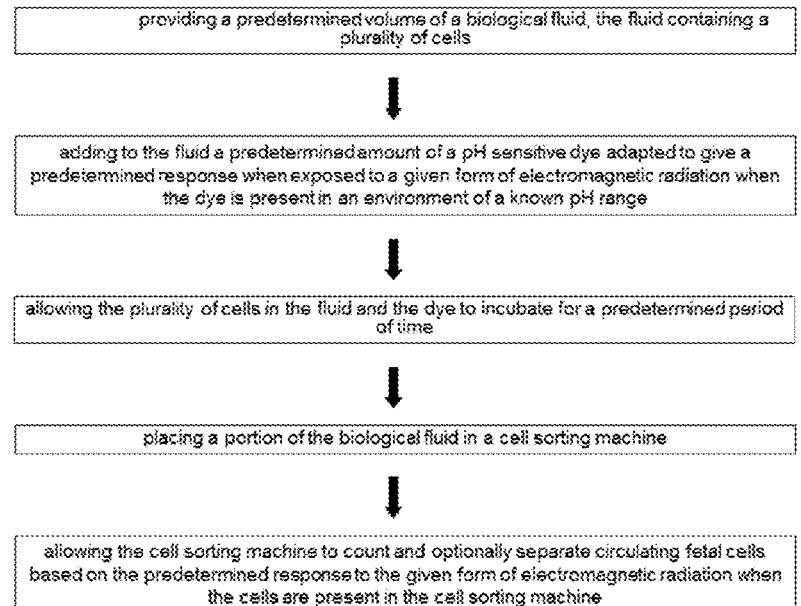
FIG. 1 shows a method according to one embodiment of the invention.
Figure 2:
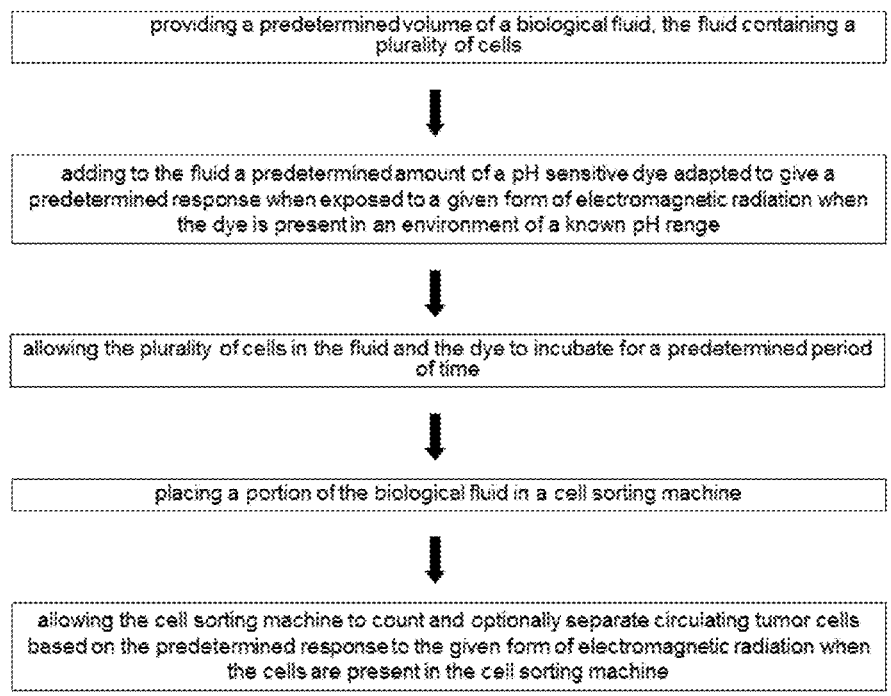
FIG. 2 shows a method according to another embodiment of the invention.

Non-limiting examples of methods according to various embodiments of the invention are shown in FIGS. 1 and 2. As another non-limiting example, FIGS. 3A-3D show schematic views of aspects of a device according to one set of embodiments. In this example, fluid sample 305 includes cells 310, where a plurality of said cells 310 are non-target cells 315 and a small percentage are target cells 320. For example, the target cells may be tumor cells, fetal cells, or other cells which are desired to be determined and/or isolated.

Figure 3A:
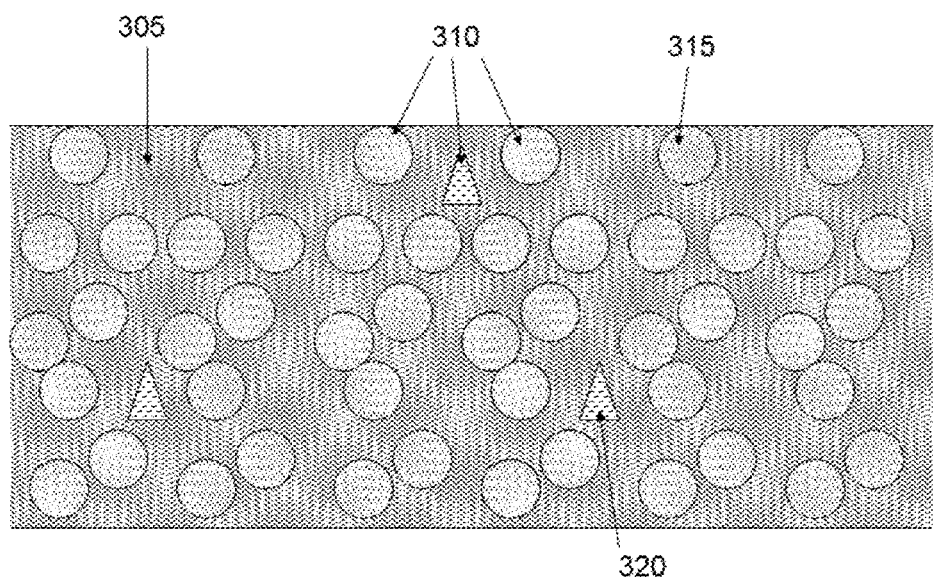
FIGS. 3A-3D shows a method according to yet another embodiment of the invention.
Figure 3B:
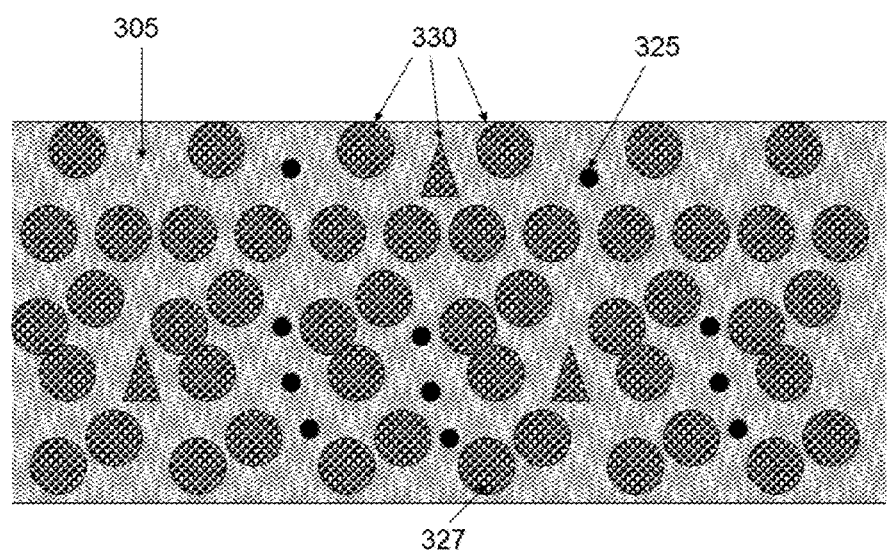

In FIG. 3B, pH-sensitive entity 325 is added to the fluid sample 305 and allowed to incubate with the fluid sample 305 for a predetermined period of time, e.g., between 1 minute and two hours. As shown in FIG. 3B, a portion of entity 325 enters cells due to the entity's ability to pass through cellular membranes. The cell-internalized pH-sensitive entity is shown as small black balls 327 in cells 330 containing the entity.

Figure 3C:
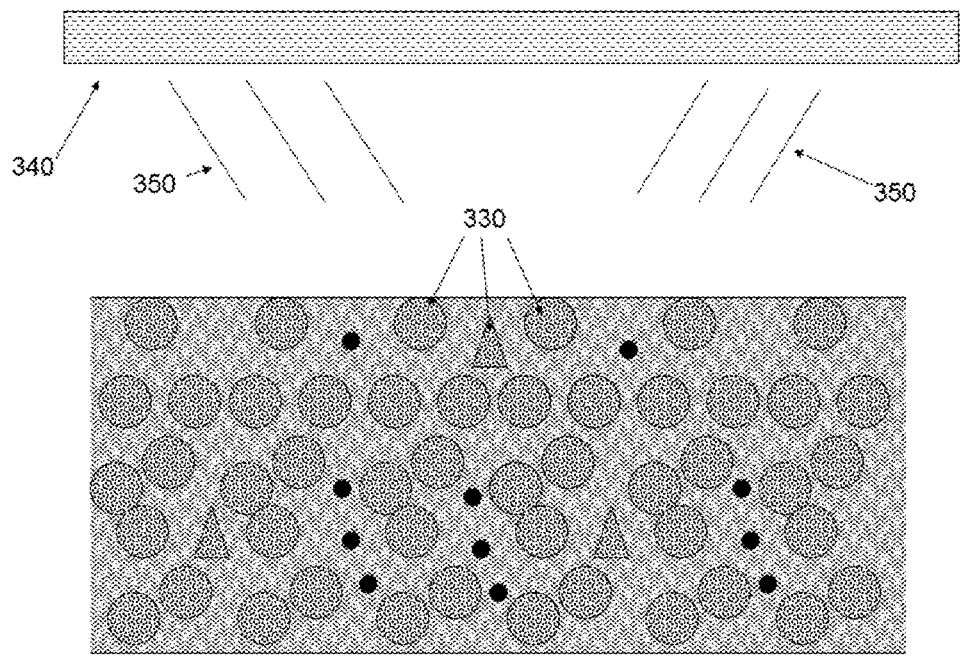
Figure 3D:
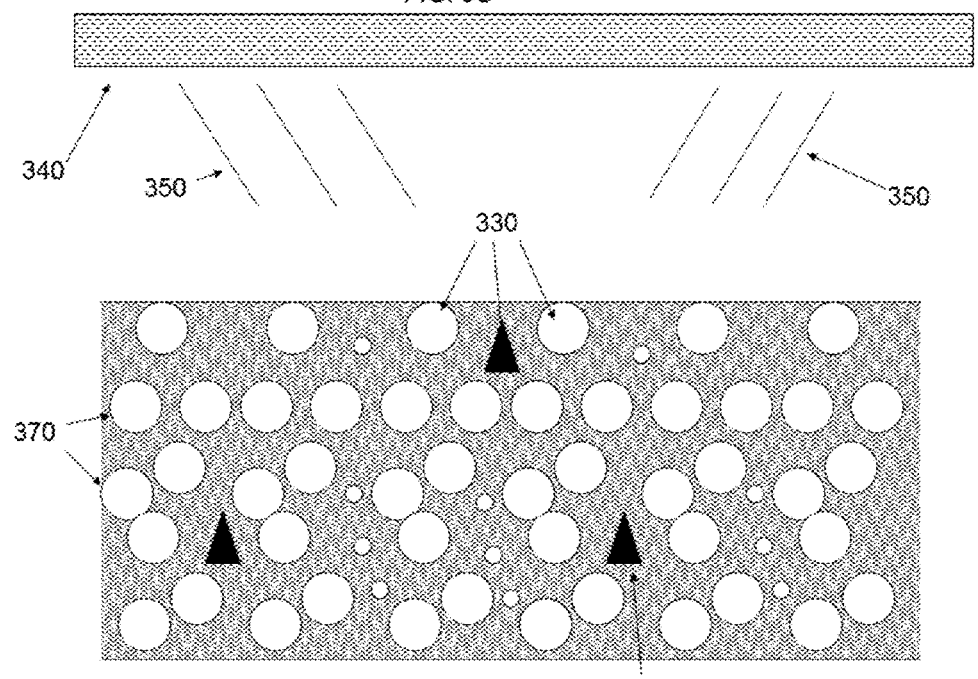

FIG. 3C shows entity-containing cells 330 in cell sorting machine 340 adapted to provide electromagnetic radiation 350 in the form of fluorescent light, in this particular example. FIG. 3D shows a view of the entity-containing cells 330 as seen after illumination with fluorescent light. Cells 360 show a predetermined color whereas the other cells 370 either show no color or show non-target color, for instance, based on the response of the entity to their intercellular pH levels. As a non-limiting example, cells 360 may fluoresce at a known wavelength when treated with a light of another, prescribed wavelength, whereas white blood cells and other cells found in the fluid sample 305 show other colors or no colors at all. Other examples are discussed herein. Determination of cells 360 allow for detection, identification, counting, sorting, and/or other manipulation of the cells, e.g., using suitable cell cytometers or the like. Subsequent analysis of the cells may include, but is not limited to, genetic analysis, morphology analysis, cytopathology analysis, or biochemical treatment.

In one set of embodiments, as discussed, a signaling molecule, or other signaling entity, is added to the fluid containing the cells or the cells are otherwise exposed to the signaling molecule or entity in some fashion. The signaling entity may be internalized by the cells, e.g., actively or passively. In some cases, once internalized, the signaling entity may change in some fashion in some of the cells (e.g., the cells of interest), while the signaling molecule may not change (or may change in a different way) in other cells. As a non-limiting example, the signaling entity may be pH-sensitive and/or may produce different "colors" or emissions at different pHs. The cells may then be determined and/or isolated using any suitable technique known in the art, based on the signaling entity, as discussed herein. For instance, in one set of embodiments, the cells may be separated using a flow cytometer or a cell sorter machine, such as a fluorescence-activated cell sorting (FACS) system. Thus, for example, cells having one intracellular pH (representing a first cell type, such as a tumor cell or a fetal cell) may be separated from cells having a different intracellular pH (representing cells of a second type, such as non-tumor or maternal cells).

Without wishing to be bound by any theory, it should be understood that certain cell types, such as cancer cells or fetal cells, may engage in metabolic behavior that significantly alters their internal cellular pH, and/or there may be other changes that modify the polarity of their cytoplasm that can be determined as changes in pH. It is believed that this is reflective of reactions and processes going on in such cells, and may thus provide information not reflected in other aspects of these cells, such as their relative size or relative abundance of certain cell membrane antigens. For example, in the case of circulating cancer cells, a change in intracellular pH may indicate the existence of specific functional attributes that may be useful for clinical applications, e.g., further indicating metastatic potential of the cells. For instance, in some cases, the intracellular pH of normal cells may be between about 6.8 and about 6.9, while the pH of the cancer cells may be higher than this; for instance, the pH of a cancer cell may be between 7.2 and about 7.4. In some cases, these pH changes may be significant, e.g., resulting in a change of at least about 0.1, at least about 0.2, at least about 0.3, at least about 0.4, at least about 0.5, at least about 0.7, at least about 1, at least about 1.2, at about 1.5, at least about 1.7, at least about 2, or more pH units, relative to normal intracellular pHs. In some cases, the pH changes may be significant. For example, there may be a change of at least about 0.5, at least about 1, at about 1.5, at least about 2, or more pH units, relative to normal intracellular pHs.

However, while some embodiments of the instant invention may be directed to the determination and/or isolation of cancer cells, tumor cells, fetal cells, etc., it should be understood that these are by way of example only, and that other cell types, e.g., exhibiting changes in pH due to enhanced metabolism, disease states, external conditions (e.g., toxins or poisons, concentration of CO or $CO_2$), or the like, may also be determined and/or isolated in other embodiments of the invention. In addition, it should also be understood that fluids other than blood may be analyzed in other embodiments of the invention; for example, the cells may be present in other fluids such as blood serum, cerebral spinal fluid, urine, nipple aspirate, phlegm, pleural abdominal exudate or transudate, amniotic fluid, saline, cell media, water, or the like. In some cases, the fluid may be one that arises biologically, e.g., from an organism such as a human. The cells may be human and/or non-human cells. For example, in one embodiment, non-human cells present within blood (or other fluid) may be separated from human cells, e.g., on the basis of intracellular pH or other conditions.

The signaling entity may generally be a material that responds to electromagnetic radiation or other energy directed at it. In some cases, the signaling entity can specifically bind to an analyte; however, in other cases, the signaling entity can bind nonspecifically or otherwise interact with various analytes, or to other species (e.g., $H^+$ in the case of some pH-sensitive entities). The signaling entity may be a single type of molecule, or a plurality of different types of molecules in some cases. Color generation or fluorescence is one of a number of possible responses including, but not limited to, energy release, or chemical reactivity. Thus, a signaling entity, as used herein, is not limited to only color changes. It should also be understood that color generally refers to any response of the entity to treatment with electromagnetic radiation. Fluorescence, light, Raman, or other quantum-related phenomena are non-limiting examples of a response that may be referred to as a "color" change. Examples of suitable electromagnetic radiation include, but are not limited to, white light, laser light at a predetermined at least one wavelength, visible light at at least one wavelength, fluorescent light, X-ray radiation, microwave radiation, etc. or a combination of different forms of electromagnetic radiation, including but not limited to any combination of any of these. Those of ordinary skill in the art will be able to readily determine suitable electromagnetic radiation based on the signaling entity used.

In addition, it should be understood that in some cases, the fluid (e.g., blood) may undergo pre-treatment with chemicals, physical conditions, etc., for example, prior to or simultaneously with the addition of one or more signaling entities. For example, the fluid may be filtered, treated with an anticoagulant (e.g., citrate or heparin), acidified, centrifuged, or the like. As another example, the fluid may be exposed to one or more buffers. In some cases, the buffers may include buffers at different pH's.

In one set of embodiments, the signaling entity is pH-sensitive. pH sensitivity, as discussed herein, includes not only the usual definition of hydrogen ion activity in solution, but also a more extended description that includes solution polarity and the like, at least in some embodiments. The pH-sensitive entity may have at least a first color (or other determinable state) at a first pH and a second color (or other determinable state) at a second pH different from the first pH. The first pH and the second pH may be separated by at least about 0.5, at least about 1, at about 1.5, at least about 2, at least about 2.5, at least about 3, at least about 4, or at least about 5 pH units. In some cases, certain cells, such as some types of cancer cells or fetal cells, may exhibit differences in intracellular pH compared to other cells, which can be detected using pH-sensitive signaling entities.

In some cases, the signaling entity may be able to permeate cellular membranes or otherwise enter a cell, e.g., into the cytoplasm. In some cases, the signaling entity can diffuse passively across a cellular membrane; in other cases, however, the signaling entity enters a cell through active processes (e.g., via phagocytosis, pinocytosis, stimulation of cell-surface receptors, or the like). The signaling entity may also be able to adapt forms and color schemes that are reflective of the pH or solvent polarity environments associated with the inner regions of such cells, and in some cases, in response to modifying molecules that may be present in such regions (e.g., enzymes). The signaling entity may be biocompatible in some fashion, although in certain cases, the signaling entity need not be biocompatible; for example, exposure of the cells to the signaling entity may injure or kill the cells, although determination of the signaling entity may still occur.

The signaling entity may be excited in some fashion, e.g., using suitable electromagnetic energy, to allow for the identification or determination of such cells, e.g., due to the unique pH-associated color found in those cells. For example, the signaling entity may exhibit fluorescence, phosphorescence, a change in absorption (e.g., at particular wavelengths), or the like. Examples of suitable electromagnetic energy include, but are not limited to, white light, laser light at a predetermined at least one wavelength, visible light at at least one wavelength, fluorescent light, X-ray radiation, microwave radiation, etc. or a combination of any of these and/or other types of electromagnetic energy.

The following are non-limiting examples of pH-sensitive entities that may be used in various embodiments: 2',7'-bis(2-carboxyethyl)-5(6)-carboxyfluorescein tetrakis(acetoxymethyl) ester (BCECF AM), 5(6)-carboxy-2',7'-dichlorofluorescein, 5(6)-carboxyfluorescein, 5(6)-carboxyfluorescein diacetate, 5(6)-carboxyfluorescein N-hydroxysuccinimide ester, 3,6-diacetoxyphthalonitrile, 6,8-dihydroxy-1,3-pyrenedisulfonic acid disodium salt, Eosin diacetate, or naphthofluorescein. Other pH-sensitive entities may also be used in some cases. In some embodiments, the pH-sensitive entity may be one whose color profile at various pH value changes, and which has some ability to enter a cell, e.g., passively or through diffusion. In some cases, the pH-sensitive entity may be one that fluoresces after undergoing chemical modification via intracellular enzymes. Many such pH-sensitive entities can be obtained commercially. However, it should be understood that the pH-sensitive entities can also include not only pH dyes per se, but also other entities that show color changes or other discriminatory behavior relative to pH or the like.

In one set of embodiments, a signaling entity (e.g., one that is pH-sensitive) may be used to distinguish a target cell of interest (e.g., a cancer cell or a fetal cell, etc.) from other surrounding cells that are not of interest (e.g., respectively, normal cells or maternal cells, or even fetal cells associated with prior pregnancy, etc.). Other examples are discussed herein. In some cases, for example, the signaling entity may have a first state in a first type of cell (e.g., the target cell) and a second state in a second type of cell (e.g., a non-target cell), where the first state and the second state are different; for instance, the first state may be fluorescent, while the second may be less fluorescent (or substantially less fluorescent).

As an example, with respect to a pH-sensitive entity, the first type of cell may have a first intracellular pH, and the second type of cell may have a second intracellular pH, where the pH's are different by at least about 0.1, at least about 0.2, at least about 0.3, at least about 0.4, at least about 0.5, at least about 0.7, at least about 1.0, at least about 1.2, at least about 1.5, at least about 1.7, at least about 2.0 pH units, or more in some cases. If the pH-sensitive entity has different states in the first and second cell types, then the cell types may be distinguished from each other, e.g., as is discussed herein.

For instance, at a first pH (e.g., the intracellular pH of a target cell), the pH-sensitive entity may be fluorescent, and at a second pH (e.g., the intracellular pH of a non-target cell), the pH-sensitive entity may be substantially less fluorescent, e.g., producing emissions at an intensity that is less than about 50%, less than about 20%, less than about 10%, less than about 5%, less than about 2%, or less than about 1% of the first pH. In some cases, the first pH and the second pH may differ by at least about 0.5 pH units, at least about 1.0 pH unit, at least about 1.5 pH units, at least about 2.0 pH units, or more in some cases. For example, the pH-sensitive entity may be fluorescent at a pH of greater than about 7.5 and substantially less fluorescent at a pH of less than about 7, the pH-sensitive entity may be fluorescent at a pH of greater than about 7 and substantially less fluorescent at a pH of less than about 6.5, the pH-sensitive entity may be fluorescent at a pH of greater than about 6.5 and substantially less fluorescent at a pH of less than about 6, the pH-sensitive entity may be fluorescent at a pH of greater than about 6 and substantially less fluorescent at a pH of less than about 5.5, etc. (In addition, in other embodiments, any of the roles discussed here may be reversed, e.g., the pH-sensitive entity may be fluorescent at a pH of a non-target cell and substantially less fluorescent at the pH of a target cell.)

By determining fluorescence of cells within a population of cells within a sample, the first and second cell types may be distinguishable from each other. In contrast, although pH-sensitive entities or other signaling entities have previously been used to study cells, such entities have not been used to distinguish different cell types form each other.

As mentioned, various embodiments of the present invention are generally directed to the determination and/or isolation of cells of interest from a population of cells. The volume of fluid containing the cells to be analyzed may be any suitable volume, for example, femtoliters, microliters, milliliters, liters, etc. In some cases, these cells may represent a very small part of the population of cells, as previously discussed. In certain embodiments, the cells may be determined, i.e., a population of cells is studied to identify whether certain cells are present, and/or how many of those cells are present. Thus, the determination may be qualitative and/or quantitative, in various applications. In certain embodiments, the cells of interest may be isolated from the population of cells. For example, these cells may be separated from the population of cells and placed at a first location (e.g., a collection chamber), while the other cells are placed at a second location (e.g., a second collection chamber), or perhaps discarded. In some cases, the isolated cells may be further analyzed, e.g., genetically, morphologically, cytopathologically, phenotypically, etc., e.g., as discussed herein. As a non-limiting example, the genetic analysis may include a search for genetic abnormalities such as chromosome defects.

According to one set of embodiments, the cells of interest may be ones that exhibit a change in intracellular pH or other internal characteristic. For example, tumor cells often exhibit varying pH's, as compared to non-tumor cells. Without wishing to be bound by any theory, it is believed that this may be due to altered metabolic states present within the tumor cells, increased metabolism of the tumor cells relative to non-tumor cells, and/or other factors. For example, tumor cells often have the ability to use anaerobic glycolysis, even if oxygen is plentiful. Such tumor cells may be able to keep their intracellular pH at an alkaline level (e.g., around 7.4), compared to normal cells, for optimal functioning of anaerobic glycolysis. This may occur even if the extracellular pH surrounding the tumor cells is relatively acidic (e.g., around a pH of 6.8), e.g., due to the production of lactate, an end product of anaerobic glycolysis. This may occur, for instance, due to activation or overexpression of $Na^+/H^+$ pumps within the tumor cells. In contrast, normal cells may have slightly acidic intracellular pH's (e.g., around 6.8), with slightly alkaline extracellular pH's (e.g., around 7.4). Thus, since the intracellular pH of tumor cells differs from the intracellular pH of normal cells, a suitable pH-sensitive entity, such as those described herein, may be used to determine or identify the tumor cells. Thus, in one set of embodiments, tumor cells may be determined and/or isolated using suitable pH-sensitive entities, or other signaling entities such as discussed herein.

Examples of cancer or tumor cells that may be determined in fluids (such as blood) include, but are not limited, lymphomas, sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, synovioma, mesothelioma, lymphangioendotheliosarcoma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, non-small cell lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia. The cancer cells present may also represent a plurality of distinct cancers, in certain cases. In addition, in some cases, the stage of cancer may be determined.

As another example, fetal cells in early gestational stages often exhibit altered intracellular pHs or metabolic states, compared to maternal cells. While rare, occasionally fetal cells may cross the placenta and enter the mother's bloodstream. These cells can be identified or determined within the mother's blood (or within other suitable fluids), e.g., due to their differences in intracellular pH, in accordance with certain embodiments of the invention. Thus, in some embodiments, the present invention is generally directed to the determination and/or isolation of fetal cells from maternal cells. In some cases, the gestational age of the fetus may be determined, e.g., less than 4 weeks, less than 5 weeks, less than 6 weeks, less than 7 weeks, less than 8 weeks, less than 9 weeks, less than 10 weeks, etc.

In addition, in one set of embodiments, the fluid may be acidified prior to (or after) exposure of the fluid to the pH-sensitive entity (or other signaling entity), e.g., to increase the acidity of the fluid (decrease the pH of the fluid). In one set of embodiments, the fluid may be acidified by exposure to a suitable acid, such as ethylenediaminetetraacetate acid, citric acid, ascorbic acid, dehydroascorbic acid, or the like. In some cases, the acids are those that are useful for preservation or to prevent blood coagulation, etc. The acid may be added in an amount able to decrease the pH of the fluid by at least about 0.2, at least about 0.3, at least about 0.4, at least about 0.5, at least about 0.7, at least about 1 pH units, or more in some cases. In some cases, the pH is not modified by more than about 3.0, about 2.5, about 2.0, about 1.5, or about 1.0 pH units. The acid may also be present in concentrations or pH's that are insufficient to cause extended or substantial cell death within the fluid.

In certain embodiments, the fluid may be acidified by waiting a sufficient time (e.g., with or without exposure to an acid); for example, the fluid may be kept in an open or closed container for at least about 3 hours, at least about 6 hours, at least about 9 hours, at least about 12 hours, at least about 18 hours, at least about 24 hours, at least about 30 hours, at least about 2 days, at least about 3 days, at least about 4 days, etc., and/or any range between any of these numbers. As a non-limiting example, a fluid such as blood may be kept in a container for between 24-30 hours. The fluid may be kept under such conditions at any suitable temperature, e.g., around body temperature (about 37° C.), around room temperature (about 25° C.), within a refrigerator (about 4° C.), etc. Without wishing to be bound by any theory, it is believed that cells within the fluid may continue to be metabolically active (e.g., producing acid by-products, such as lactic acid), or consume oxygen and/or produce carbon dioxide (which may form carbonic acid within the fluid), which may facilitate acidification of the fluid. Thus, in certain embodiments, the fluid may be acidified by waiting for a sufficient time.

Without wishing to be bound by any theory, it is believed that, somewhat counter-intuitively, acidification of the fluid may promote the ability to determine or distinguish target cells from other non-target cells within the fluid using a pH-sensitive entity, at least in certain embodiments of the invention. It is believed that certain cell types, such as cancer cells or fetal cells, are metabolically active and/or have the ability to resist acidification to a greater degree than other types of cells. For example, cancer cells often exist in relatively acidic environments with poor or insufficient blood flow, and hence may exhibit more efficient mechanisms at controlling the intracellular pH even when the extracellular pH is acidic. Fetal cells may also be more metabolically active and thus be able to resist acidification to a greater extent than maternal cells. Accordingly, by acidifying the fluid, cells of interest that can resist acidification can be more readily determined or distinguished, compared to other cells that cannot resist acidification to the same degree. Thus, even though a pH-sensitive entity is used in certain embodiments, the fluid may also be acidified, before and/or after exposure of the fluid to the pH-sensitive entity.

Once exposed to a suitable signaling entity, such as a pH-sensitive entity, cells exhibiting a first characteristic (such as a first pH, e.g., an intracellular pH) may be determined and/or isolated from cells exhibiting a second characteristic (such as a second pH, e.g., an intracellular pH). Many techniques for separating cells on the basis of a signaling entity are available. For example, in some embodiments, a cell sorting machine may be used. Cell sorting machines may include flow cytometry devices and the like. A cell cytometer or a flow cytometer generally describes a machine capable of identifying, determining, and/or counting cells based on a signal emitted from the cells. Cell cytometers, amongst other devices, allow rapid determination or counting of cells based on a differential response to, e.g., electromagnetic radiation. The count of cells may be reported using any suitable technique, for example, as absolute numbers (e.g., number of cells), as a density (e.g., count in a given volume of biological fluid), in proportion to other cells in the same fluid, or the like. This may suitable in some applications, e.g., for clinical purposes, assessing metastatic potential of tumor cells, or the like.

Cell cytometers may also include additional component to further sort cells based on such response, in certain instances. For example, the cell cytometer may incorporate multiple detection stages to provide negative or positive selection of cells. Computing devices and other elements may also be used for control of processes, as well as for data analysis and storage, in some cell sorting machines. Examples include a mobile computing device, smartphone, cellular phone, tablet computer, laptop computer, or tabletop computer. Cell sorting machines may also be fixed or mobile. Many such cell sorting machines are readily available commercially. The cell sorter machine may also be used in conjunction with suitable pre-treatment steps in various embodiments, e.g., a step to first remove certain cell fractions, e.g., red blood cell, using a device, a filter, or the like.

In some embodiments, the cell sorting machine may incorporate more than one detection stage, e.g., to provide negative or positive selection of cell types, to further improve isolation of cells, etc. For example, in some cases, antibodies may be used for detection. The antibodies may be free or attached to a magnetic particle, such as a nanoparticle. As a specific non-limiting example, antibodies for CD45 may be used to further isolate leukocytes from a pH-responsive isolate of cells in order to enhance the fraction of tumor cells in the isolated cell fraction. In some cases, the cells may be exposed to antibodies able to recognize a tumor-specific antigen, such as EpCAM, EphB4, HER2, EGFR, CEA, MUC-1, CD45, or other tumor-specific antigens known to those of ordinary skill in the art. In some cases, the antibodies are organ-specific antibodies, e.g., for determining the location of a tumor. For instance, the antibodies may be used for immunostaining purposes.

In another set of embodiments, determination of cells and/or sorting may occur using fluorescence microscopy. For instance, in one set of embodiments, the cells may be positioned slides, petri dishes, etc. for analysis using a fluorescence microscope. In some cases, this process may be automated or semi-automated. For example, a plurality of cells may be analyzed or automatically screened using a fluorescence microscope to determine which cells are fluorescent and which cells are not fluorescent (or are less fluorescent), e.g., as discussed herein. A person may analyze the fluorescence of the cells, or in some cases, the images may be analyzed using a computer programmed with appropriate image analysis techniques. Many such programs for image analysis of fluorescent samples are commercially available.

As another non-limiting example, an additional separation step may use antibodies able to recognize certain cell antigens. For example, the antibody may recognize cell antigens such as CD4, CD8, CD45, CD71, anti-eplison globin, or the like. As an example, the cells may be exposed to antibodies for fetal hemoglobin, thus separating fetal red blood cells from the initial isolated cell fraction based on pH. The remaining cells in that fraction may further be isolated using, for instance, CD4 and CD8 antibodies; e.g., further selecting either cells negative for both CD4 and CD8 or positive for both CD4 and CD8 would provide for further isolation of fetal white cells. Negative selection for single positive cells (single positive or for CD4 or for CD8) also can be used in some cases.

It should be understood that in some cases, the devices or methods discussed herein may be fully or partially integrated into one or more devices, including human diagnostic equipment. It should also be understood that some embodiments could allow for measurement of many samples either sequentially or simultaneously, and single experiments discussed herein are for convenience only and are not intended to be limiting.

The following examples are intended to illustrate certain embodiments of the present invention, but do not exemplify the full scope of the invention.

Example 1

In this example, it was demonstrated that human cancer cells in peripheral blood could be identified and isolated, exploiting their preferential maintenance of a more basic pH level than their surrounding media or other blood borne cells. In this example, a pH-sensitive fluorescent dye was added to carcinoma cells and normal blood cells, and the fluorescent signal corresponding to the dye internalized in cells with more basic pH was used for detection, counting, and potential separation in a flow cytometer or sorter machine. In the present example, a fluorescence-activated cell sorting (FACS) system was used. The sorted cells were presented in a well-preserved state, which allowed following cytopathological and genetic analyses.

HT29 cells (human colon carcinoma) were obtained from ATCC, and 2 ml of whole normal human blood was collected from a healthy volunteer. Blood was processed within 2 hours of collection and examined by a BD FACSARIA II SORP sorter machine following incubation with a fluorescent dye (BCECF AM), and also in certain experiments, also without such an incubation step. Blood was processed with RBC lysis and also without RBC lysis steps in different experiments. Finally, blood was mixed with colon carcinoma cells (HT29) and incubated with BCECF AM in some experiments as described herein.

1 mg of BCECF AM (Invitrogen) was dissolved in 1 ml of DMSO and 10 aliquots were prepared. One aliquot was dissolved in 10 ml of Hank's balanced salt solution in order to make a working solution (0.016 mM). The working solution of BCECF AM was added to the samples (2 ml of BCECF AM to 2 ml of sample), and incubated in room temperature for one hour. Lysis of the RBCs then was performed, after staining by fluorescent dye (BCECF AM) by adding to the sample 1 ml of RBC lysis buffer (BioLegend) dissolved in 10 ml of distillate water and incubated for 10 minutes in room temperature. PBS was then added up to 50 ml total volume, followed by centrifugation (2000 rpm for 10 min) and removal of the supernatant. 2 ml of each sample was introduced for analysis by a BD FACSARIA II SORP machine and the data was analyzed using the BD FACSARIA II SORP system software. HT29 cells were further sorted and isolated in a tube containing 70% ethanol.

Figure 4A:
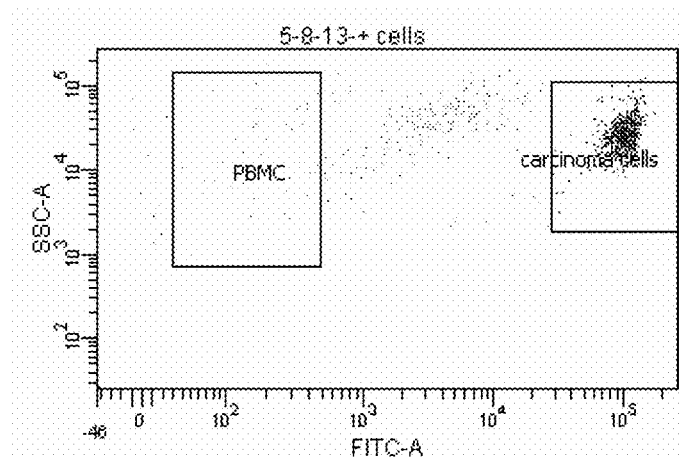
FIGS. 4A-4H show experiments using HT29 cells, in accordance with certain embodiments of the invention.
Figure 4B:
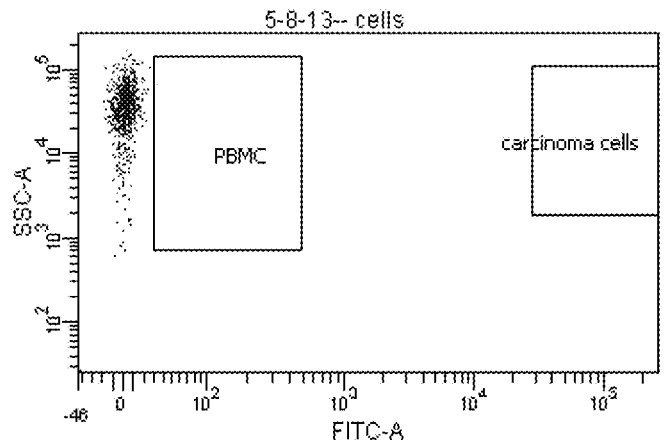
Figure 4C:
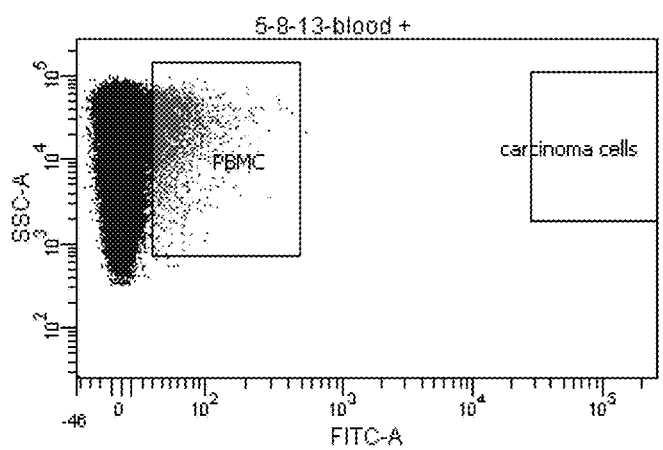

FIG. 4A shows HT29 cells alone, incubated with BCECF AM (0.016 M) for one hour at room temperature, showing strong fluorescence of HT29 cells. In this and the following figures showing data obtained from the FACS software, the abscissa (FITC-A) always refers to the strength of the fluorescent signal obtained from the cell, and the ordinate (SSC-A) is an area parameter useful for rejection of doublet cells. Both axes are logarithmic. FIG. 4B shows HT29 cells alone, without adding of BCECF AM, showing weak fluorescence of HT29 cells. FIG. 4C shows blood without lysis and incubated with BCECF AM (0.016 mM) for one hour at room temperature, showing a weak fluorescent signal. FIG.

Figure 4D:
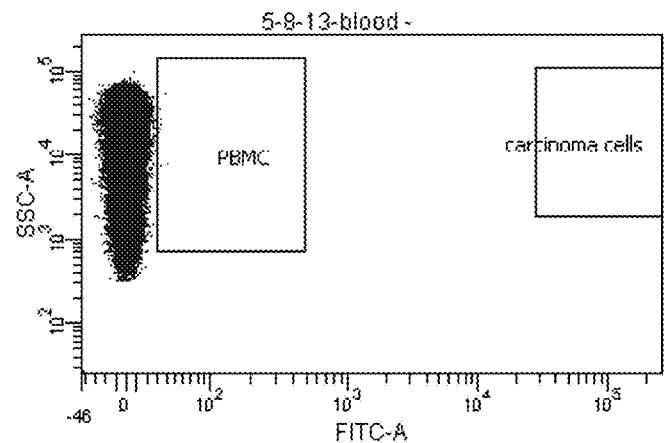
Figure 4E:
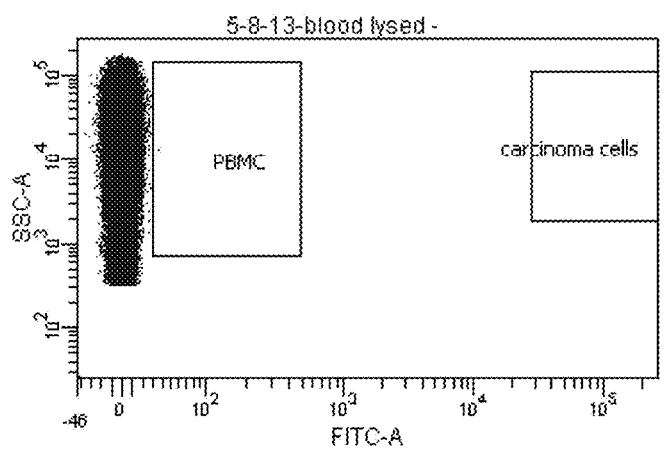
Figure 4F:
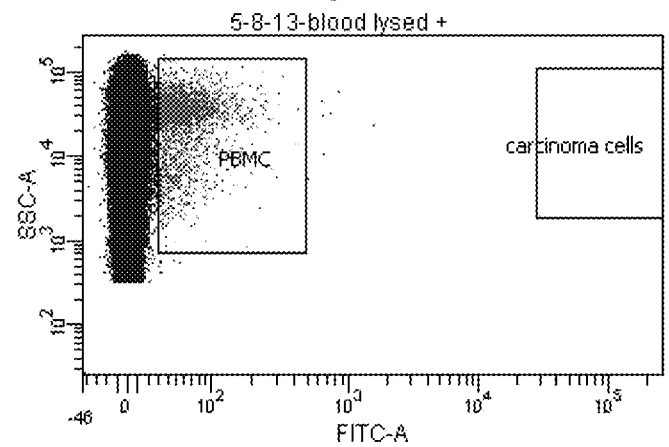
Figure 4G:
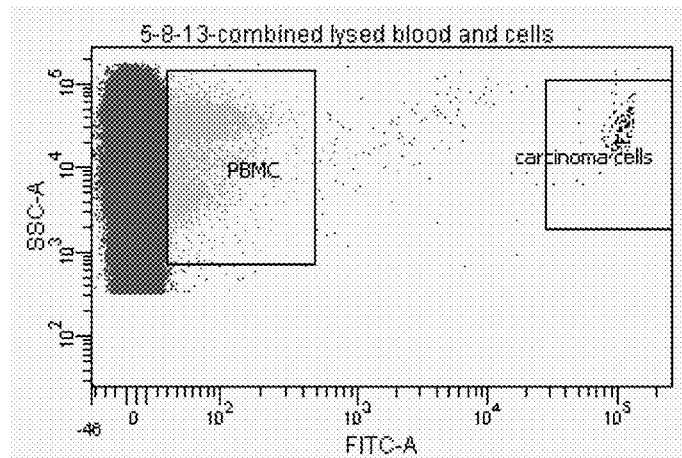
Figure 4H:
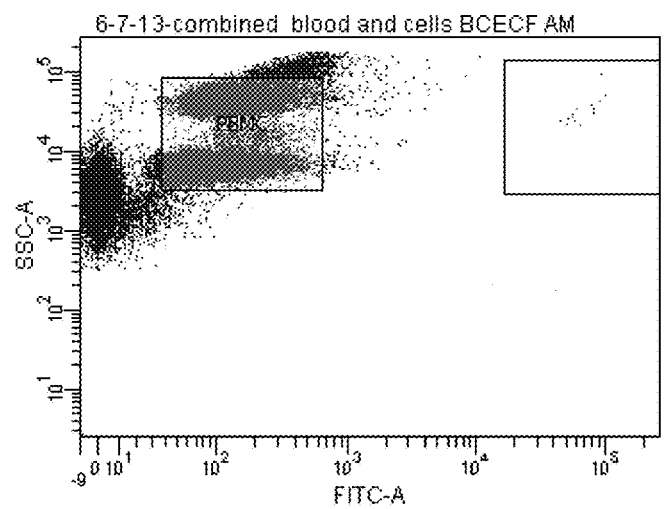

4D shows blood without lysis and without adding of BCECF AM, showing almost no fluorescence. FIG. 4E shows blood with RBC lysis and without adding of BCECF AM, showing almost no fluorescence. FIG. 4F shows blood alone, with RBC lysis and incubation with BCECF AM (0.016 mM) for one hour at room temperature, showing a weak fluorescent signal. FIG. 4G shows a mixture of blood with RBC lysis and HT29 cells incubated with BCECF AM (0.016 mM) for one hour at room temperature. HT29 cells show much stronger fluorescent signal then blood cells, and could then be detected and sorted in the FACS sorter machine. FIG. 4H demonstrates reproducibility by repeating the procedures of this example with a separate, independent sample.

This example demonstrates: (1) isolated carcinoma cells showed strong fluorescent signal when incubated with a basic pH-sensitive fluorescent dye (FIG. 4A); (2) isolated carcinoma cells did not show strong fluorescent signal naturally without being incubated with same dye (FIG. 4B); (3) normal circulating blood cells did not show strong fluorescent signal when incubated with the same dye (FIG. 4C); (4) normal circulating blood cells did not show strong fluorescent signal without being incubated with same dye (FIG. 4D); (5) normal circulating blood in which red blood cells (RBC) were lysed did not show strong fluorescent signal without being incubated with same dye (FIG. 4E); (6) normal circulating blood in which RBC were lysed did not show strong fluorescent signal after being incubated with same dye (FIG. 4F); (7) a mixture of normal circulating blood with lysed RBC with isolated carcinoma cells could be separated in a FACS sorter after incubation with a basic pH-sensitive fluorescent dye (FIG. 4G); and (8) repeatability of these experiments produced similar results (FIG. 4H).

Example 2

In this example, it was demonstrated that embryonic cells in peripheral blood could be identified and isolated, exploiting their preferential maintenance of a more basic pH level than their surrounding media or other blood borne cells. In this example, a pH-sensitive fluorescent dye was added to embryonic cells and normal blood cells, and the fluorescent signal corresponding to the dye internalized in cells with more basic pH was used for detection, counting, and potential separation in a flow cytometer or sorter machine. In the present example, a fluorescence-activated cell sorting (FACS) system was used. The sorted cells were presented in a well-preserved state, which allowed following cytopathological and genetic analyses.

Embryonic mouse hypothalamic cells were obtained from Cellutions Biosystems, Inc., and 2 ml of whole blood was collected from a healthy human volunteer. The blood was mixed with embryonic cells. Blood was processed within 2 hours of collection and examined by a BD FACSARIA II SORP machine following incubation of a fluorescent dye: BCECF AM, and also in certain experiments, without such incubation step.

1 mg of BCECF AM (Invitrogen) was dissolved in 1 ml of DMSO and 10 aliquots were prepared. One aliquot was then dissolved in 10 ml of Hank's balanced salt solution in order to make a working solution with concentration of 0.016 mM. The working solution was added of BCECF AM to the samples (2 ml of BCECF AM to 2 ml of sample), and incubated at room temperature for one hour. Lysis of the RBCs then was performed, after staining by fluorescent dye (BCECF AM), by adding to the sample 1 ml of RBC lysis buffer (BioLegend) dissolved in 10 ml of distillate water and incubated for 10 minutes at room temperature. PBS was then added to result in up to 50 ml of total volume, followed by centrifugation (2000 rpm for 10 min) and removal of the supernatant.

2 ml of each sample was then introduced for analysis by a BD FACSARIA II SORP machine and the data analyzed by the BD FACSARIA II SORP system software. Embryonic cells were further sorted and isolated in a tube containing 70% ethanol. Isolated embryonic cells were placed on an optical microscope slide and viewed at 40× (FIG. 5C). For comparison, white blood cells were also viewed at 40× (FIG. 5D).

Figure 5A:
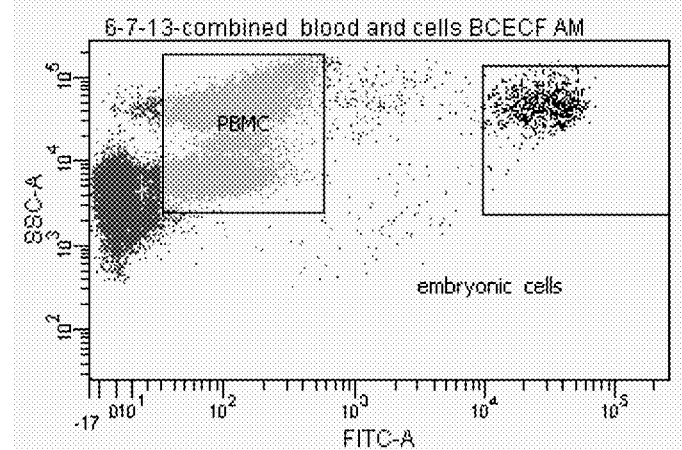
FIGS. 5A-5D show experiments using lysed blood mixed with embryonic cells, according to some embodiments of the invention.
Figure 5B:
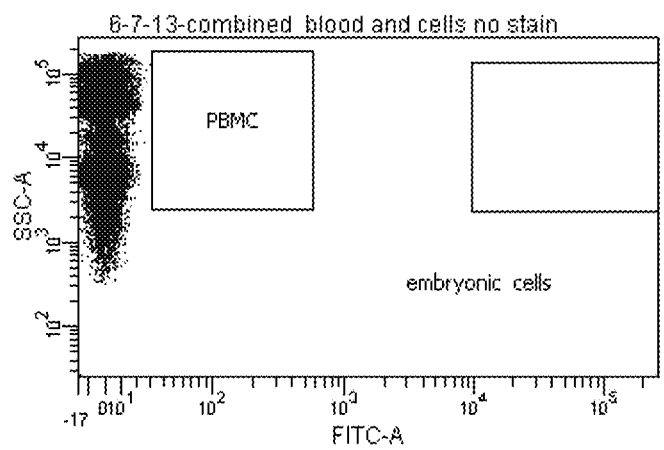
Figure 5C:
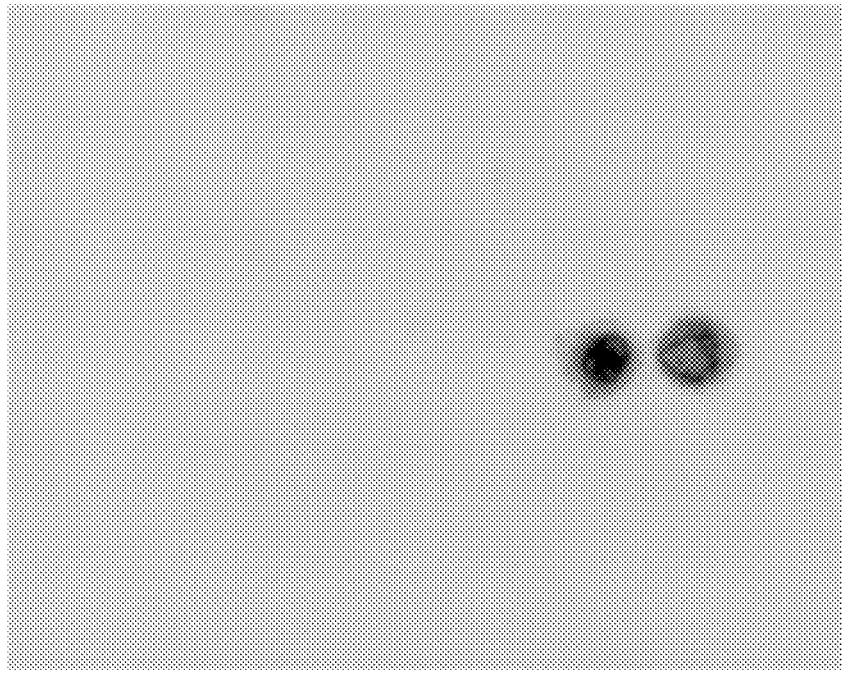
Figure 5D:
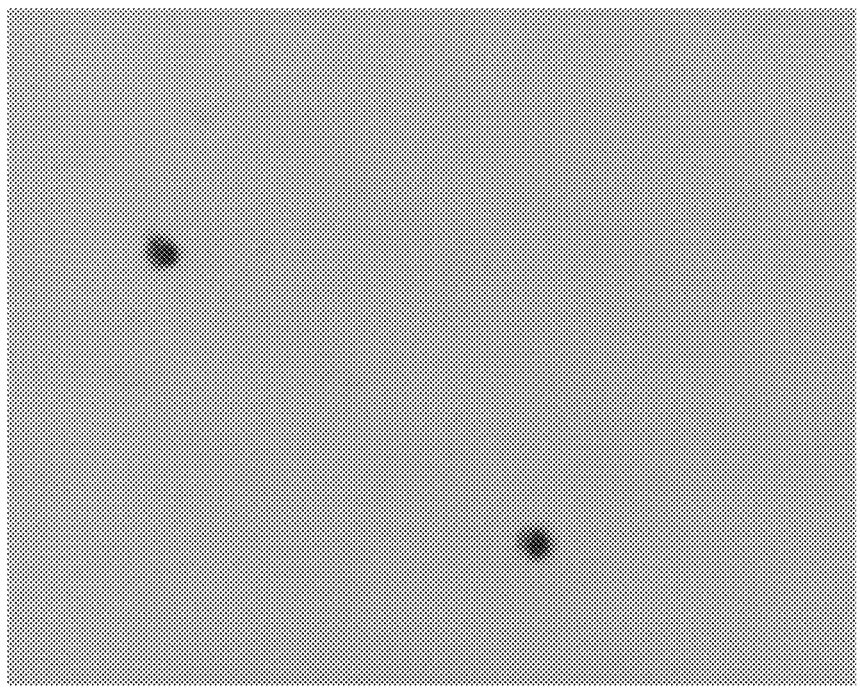

FIG. 5A shows lysed blood mixed with embryonic cells incubated with BCECF AM (0.016 mM) for one hour at room temperature, demonstrating that embryonic cells have much stronger fluorescence than other blood cells, which could be exploited for detection, counting, and/or sorting. FIG. 5B shows lysed blood mixed with embryonic cells without adding of BCECF AM, showing almost no fluorescence. FIG. 5C shows embryonic cells isolated using techniques of the present invention viewed at 40× magnification. FIG. 5D shows white blood cells viewed at 40× magnification for comparison purposes.

This example demonstrated: (1) a mixture of normal circulating blood with lysed RBC with embryonic cells could be separated in a FACS sorter after incubation with a basic pH-sensitive fluorescent dye (FIG. 5A); and (2) a mixture of normal circulating blood in which RBC were lysed with embryonic cells did not show strong fluorescent signal without being incubated with same dye (FIG. 5B).

Example 3

In this example, it was demonstrated that circulating cancer cells in peripheral blood obtained from a cancer patient could be identified and isolated, exploiting their preferential maintenance of a more basic pH level than their surrounding media or other blood borne cells. In this example, a pH-sensitive fluorescent dye was added to a sample of a cancer patient blood, and the fluorescent signal corresponding to the dye internalized in cells with more basic pH was used for detection, counting, and potential separation in a flow cytometer or sorter machine. In the present example, a fluorescence-activated cell sorting (FACS) system was used. The sorted cells are presented in a well-preserved state, enabling subsequent cytopathological and genetic analyses.

2 ml of whole blood was collected from a cancer patient with prior diagnosis of stage 4 Hodgkin lymphoma, following consent using an informed consent declaration. 2 ml of whole normal human blood was also collected from a healthy volunteer. Blood was processed within 2 hours of collection and examined by a BD FACSARIA II SORP machine following incubation of a fluorescent dye (BCECF AM).

1 mg of BCECF AM (Invitrogen) was dissolved in 1 ml of DMSO and 10 aliquots were prepared. One aliquot was dissolved in 10 ml of Hank's balanced salt solution in order to make a working solution (0.016 mM). The working solution of BCECF AM was added to the samples (2 ml of BCECF AM to 2 ml of sample) and incubated at room temperature for one hour. Lysis of the RBCs then was performed following staining by fluorescent dye (BCECF AM) by adding to the sample 1 ml of RBC lysis buffer (BioLegend) dissolved in 10 ml of distillate water and incubated for 10 minutes at room temperature. PBS was then added to result in up to 50 ml total volume, followed by centrifugation (2000 rpm for 10 min) and removal of the supernatant.

2 ml of each sample was introduced for analysis by a BD FACSARIA II SORP machine and the data analyzed by the system BD FACSARIA II SORP software. Hodgkin lymphoma cells were further sorted, stained by H&E stain (hematoxylin and eosin stain), and isolated on the microscope glass slide and viewed at 40× (FIG. 6C).

Figure 6A:
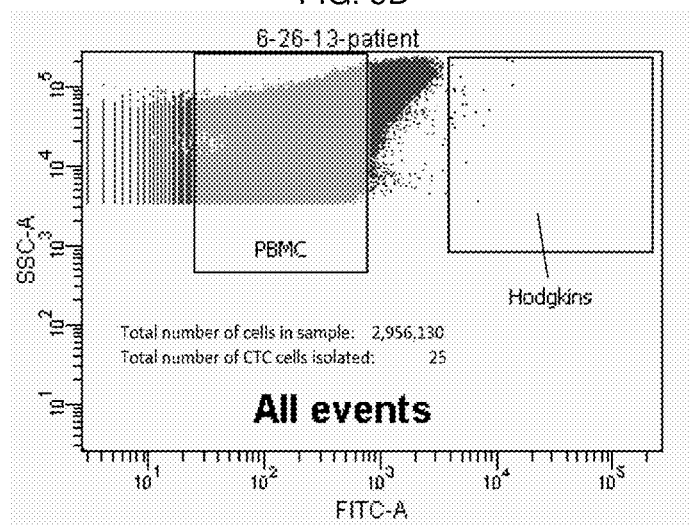
FIGS. 6A-6C show circulating cancer cells isolated in accordance with certain embodiments of the invention.
Figure 6B:
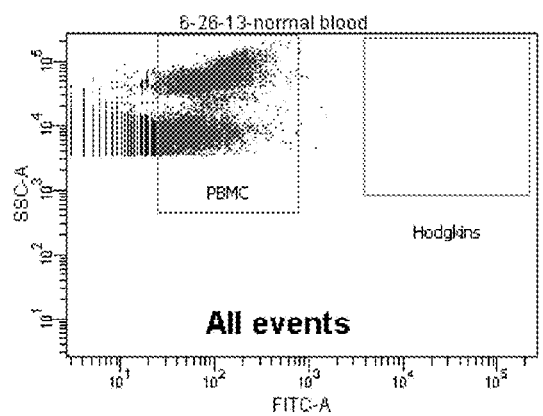
Figure 6C:
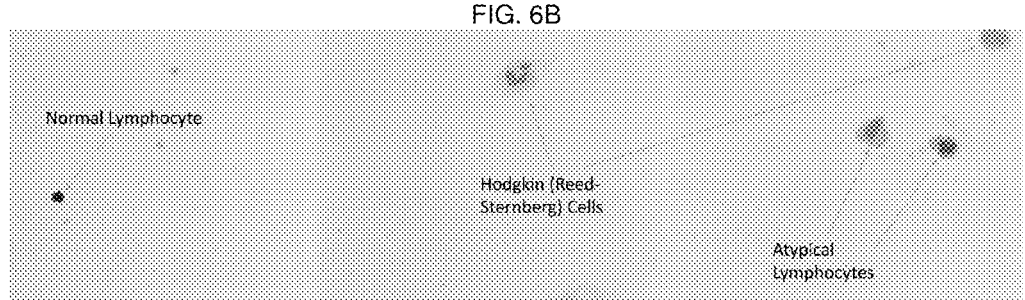

FIG. 6A shows blood from the cancer patient with RBC lysis and staining by BCECF AM (0.016 mM) for one hour at room temperature, demonstrating that cancer cells have a stronger level of fluorescence, allowing their detection, identification, counting, and sorting for later analyses. FIG. 6B shows blood from the healthy volunteer with RBC lysis and staining by BCECF AM (0.016 mM) for one hour at room temperature. FIG. 6C shows circulating cancer cells that were isolated, and normal lymphocytes, viewed at 40× magnification.

This example demonstrated: (1) circulating cancer cells in a blood sample from a cancer patient with lysed red blood cells, could be separated in a FACS sorter after incubation with a basic pH-sensitive fluorescent dye (FIG. 6A); and (2) a blood sample from healthy volunteer with lysed RBC after incubation with the same basic pH-sensitive fluorescent dye showed almost no cells with high fluorescence level, indicating lack of circulating cancer cells (FIG. 6B).

Example 4

This example demonstrated that human cancer cells in peripheral blood may be identified and isolated, exploiting their preferential maintenance of a more basic pH level than their surrounding media or other blood borne cells. In this example, the generality was further illustrated by the use of a different (5(6)-carboxyfluorescein) pH-sensitive fluorescent dye, which was added to carcinoma cells and normal blood cells. The fluorescent signal corresponding to the dye internalized in cells with more basic pH was then used for detection, counting, and potential separation in a flow cytometer or sorter machine. In the present example, a fluorescence-activated cell sorting (FACS) system was used. The sorted cells were presented in a well-preserved state, which allowed following cytopathological and genetic analyses.

HT29 cells (human colon carcinoma) were obtained from ATCC and 2 ml of whole normal human blood was collected from healthy volunteer. Blood was processed within 2 hours of collection, mixed with carcinoma cells and examined by a BD FACSARIA II SORP machine following incubation of a fluorescent dye: 5(6)-carboxyfluorescein. Blood was processed with RBC lysis. 1 g of 5(6)-carboxyfluorescein (Sigma Aldrich) was dissolved in 100 ml of distillate water, a saturated solution in water was produced, and 10 aliquots were prepared.

Lysis of the RBCs then was performed, after staining by fluorescent dye (5(6)-carboxyfluorescein) by adding to the sample 1 ml of RBC lysis buffer (BioLegend) dissolved in 10 ml of distillate water and incubated for 10 minutes at room temperature. PBS was then added up to 50 ml total volume, followed by centrifugation (2000 rpm for 10 min) and removal of the supernatant.

2 ml of each sample was introduced for analysis by a BD FACSARIA II SORP machine and the data analyzed by the system software. HT29 cells were further sorted and isolated on the glass slide for microscopy. The slide was stained according to standard H&E protocol.

Figure 7A:
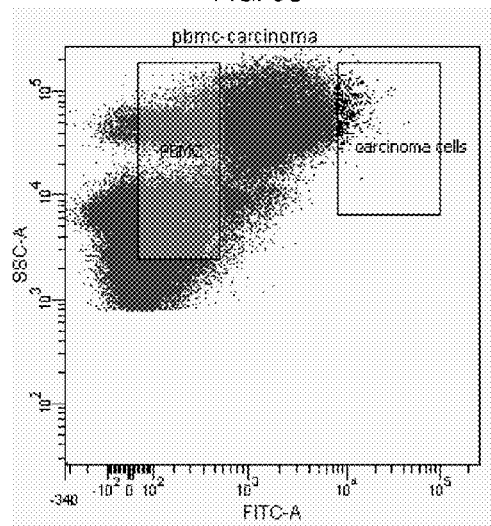
FIGS. 7A-7C show a mixture of blood with RBC lysis and HT29 cells, in accordance with some embodiments of the invention.
Figure 7B:
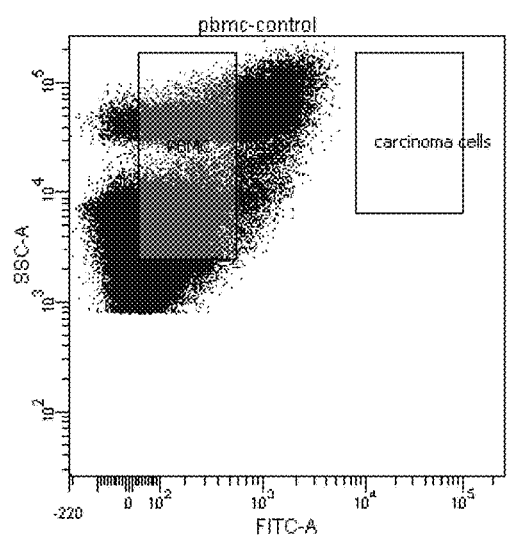
Figure 7C:
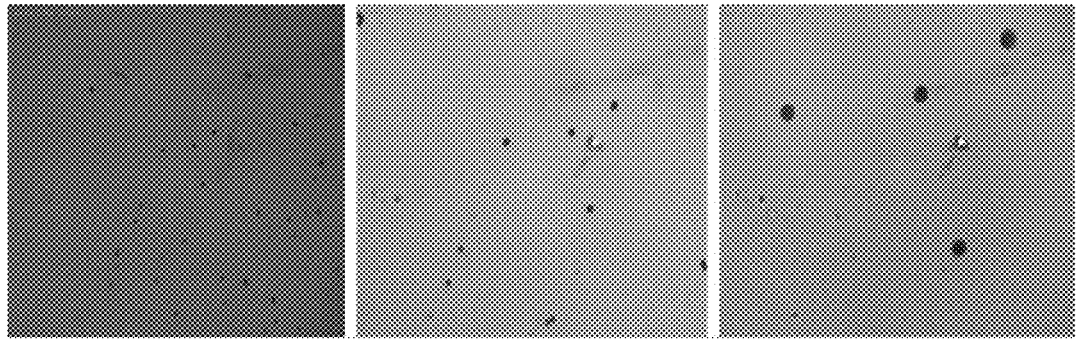

FIG. 7A shows a mixture of blood with RBC lysis and HT29 cells incubated with 5(6)-carboxyfluorescein for 30 minutes at room temperature. HT29 cells showed a much stronger fluorescence signal then blood cells, and could be detected and sorted in the FACS sorter machine. FIG. 7B shows blood alone, with RBC lysis without HT29 cells incubated with 5(6)-carboxyfluorescein for 30 minutes at room temperature. This example does not have a high fluorescence cell population, corresponding to carcinoma cells, present in previous figure. FIG. 7C shows circulating cancer cells that were isolated, and viewed at different magnifications (same region).

This example demonstrated: (1) a mixture of normal circulating blood with lysed RBC with isolated carcinoma cells could be separated in a FACS sorter after incubation with a basic pH-sensitive fluorescent dye (FIG. 7A); and (2) a normal circulating blood with lysed RBC without carcinoma cells shows no positive (high fluorescents) cells population corresponding to carcinoma cells, after incubation with the same dye (FIG. 7B). This example further demonstrated that the methods of the instant invention were not limited to any specific composition of the fluorescent dye or any other reporter molecule, and that any molecule that could provide pH-specific signal may be utilized.

Example 5

This example demonstrated that human cancer cells in peripheral blood could be identified and isolated, exploiting their preferential maintenance of a more basic pH level than their surrounding media or other blood borne cells. This example also demonstrated that treatment of the sample of cells, before staining by a pH-sensitive fluorescent dye, using a low pH buffer could modify the outcome of the test, and depending on the specific application and properties of the cells, could be used to further improve the selectivity of the present invention. In this example, pH-sensitive fluorescent dye was added to carcinoma cells and normal blood cells, after pretreatment with low pH buffer and without such pretreatment and the fluorescent signal corresponding to the dye internalized in cells with more basic pH is used for detection, counting, and potential separation in a flow cytometer or sorter machine. In the present example, a fluorescence-activated cell sorting (FACS) system was used.

HT29 cells (human colon carcinoma) were obtained from ATCC and 2 ml of whole normal human blood was collected from healthy volunteer. Blood was processed within 2 hours of collection, mixed with carcinoma cells and examined by a BD FACSARIA II SORP machine following incubation of a fluorescent dye (BCECF AM). Blood was processed with RBC lysis.

Treatment of one of the samples by low pH buffer was done by adding of 20 ml of Acetate buffer solution pH 4.6 (Sigma-Aldrich) diluted 1:20 in distillate water for 10 minutes at room temperature. PBS was then added up to 50 ml total volume, followed by centrifugation (2000 rpm for 10 min) and removal of the supernatant.

1 mg of BCECF AM (Invitrogen) was dissolved in 1 ml of DMSO and 10 aliquots were prepared. One aliquot was dissolved in 10 ml of Hank's balanced salt solution in order to make a working solution (0.016 mM). The working solution of BCECF AM was added to samples (2 ml of BCECF AM to 2 ml of sample) and incubated at room temperature for 30 minutes.

Lysis of the RBCs then was performed, after staining by fluorescent dye BCECF AM by adding to the sample 1 ml of RBC lysis buffer (BioLegend) dissolved in 10 ml of distillate water and incubated for 10 minutes at room temperature. PBS then was added up to 50 ml total volume, followed by centrifugation (5000 rpm for 10 min) and removal of the supernatant. 2 ml of each sample was introduced for analysis by a BD FACSARIA II SORP machine and the data analyzed by the system software.

Figure 8A:
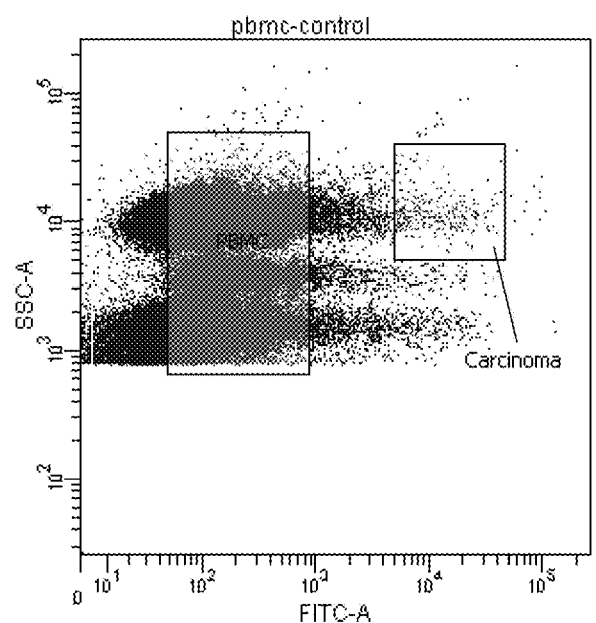
FIGS. 8A-8B show a mixture of blood with RBC lysis and HT29 cells incubated with BCECF AM, according to certain embodiments of the invention.
Figure 8B:
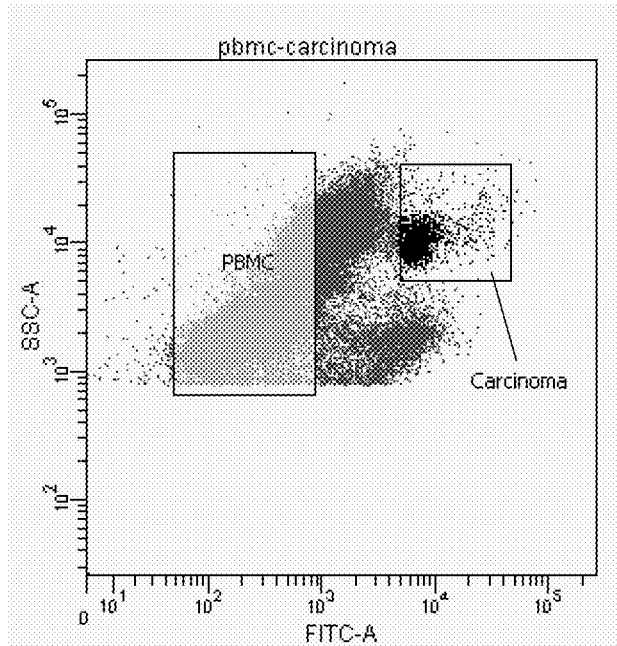

FIG. 8A shows a mixture of blood with RBC lysis and HT29 cells incubated with BCECF AM for 30 minutes at room temperature. HT29 cells showed stronger fluorescent signal than blood cells, and could then be detected and sorted by the FACS sorter machine. FIG. 8B shows a mixture of blood with RBC lysis and HT29 cells treated by low pH buffer and incubated with BCECF AM for 30 minutes at room temperature. HT29 cells showed much more solid and homogeneous population in comparing with the sample without low pH buffer treatment. At the same time, normal blood cells population showed a shift to right, corresponding to more alkaline intracellular pH in comparing with the sample without low pH buffer treatment.

This example demonstrated: (1) a mixture of normal circulating blood with lysed RBC without treatment by low pH buffer with isolated carcinoma cells could be separated in a FACS sorter after incubation with a basic pH-sensitive fluorescent dye (FIG. 8A); and (2) a normal circulating blood with lysed RBC with isolated carcinoma cells treated by low pH buffer showed changes in fluorescence cells population corresponding to carcinoma cells and normal blood cells, after incubation with the same dye (FIG. 8B).

Example 6

This example demonstrated that fetal/embryonic cells in peripheral mother blood could be identified and isolated, exploiting their preferential maintenance of a more basic pH level than their surrounding media or other blood borne cells. In this example, a pH-sensitive fluorescent dye was added to peripheral blood of pregnant women, and the fluorescent signal corresponding to the dye internalized in cells was significantly higher for cells with more basic pH. This signal was then used for detection, counting, and potential separation in a flow cytometer or sorter machine. In the present example, a fluorescence-activated cell sorting (FACS) system was used. Verification that the fraction of cells separated did contain fetal cells was performed using PCR techniques for presence of a Y chromosome (PrimerDesign, h-Y-DNA PCR). Since it was expected that about 50% of the samples should contain the Y chromosome (for a sample size of sufficient statistical significance), and none of the maternal cells should have that chromosome, its subsequent identification in the isolated cell fraction in the FACS machine may be used to demonstrate the isolation of fetal cells in maternal blood.

3 ml of whole blood was collected from six pregnant women, with pregnancy status confirmed by HCG testing and additionally age of gestation by ultrasound, following consent by an Institutional Review Board approved study at a clinical site (Planned Parenthood of Southern New England, New Haven, Conn.). The de-identified samples were arbitrarily marked 001, 002, 003, 004, 005, and 006. Blood was processed within 6 hours of collection and examined by a BD FACSARIA II SORP cell sorting machine, following incubation with a fluorescent dye (BCECF AM). Another 4 samples, 3 ml each, were collected from pregnant women with pregnancy confirmed by HCG testing and ultrasound as described before, following consent by an Institutional Review Board approved study at a clinical site (Planned Parenthood of Southern New England, New Haven, Conn.). The samples were arbitrarily marked 007, 008, 009, and 010. Blood was kept at 4° C. overnight and then processed using the same protocol as the first set of samples.

1 mg of BCECF AM (Invitrogen) was dissolved in 1 ml of DMSO and 10 aliquots were prepared. 3 aliquots were dissolved in 10 ml of Hank's balanced salt solution in order to make a working solution (0.016 mM). The working solution of BCECF AM was added to samples (3 ml of BCECF AM to 3 ml of sample) and incubated at room temperature for 40 minutes. Lysis of the RBCs then was performed, after staining by fluorescent dye (BCECF AM), by adding to the sample 20 ml of RBC lysis buffer (BioLegend) to each sample (2 ml of buffer was dissolved in 20 ml of distillate water and incubated with a blood sample for 10 minutes at room temperature). PBS was then added to result in a total volume of 50 ml, followed by centrifugation (2000 rpm for 10 min) and removal of the supernatant.

2 ml of each sample was introduced for analysis by a cell sorter (BD FACSARIA II SORP) and the data analyzed by the system software. Fetal/embryonic cells were further sorted and isolated in a tube containing 1 ml of PBS. The sorted samples were underwent PCR analysis for the human Y chromosome. Samples 003, 004, and 007 were found positive by qualitative PCR for human Y chromosome.

This example demonstrated: (1) six blood samples from pregnant women in early pregnancy with lysed mother RBC were collected, and that fetal/embryonic cells could be separated in a FACS sorter after incubation with a basic pH-sensitive fluorescent dye; (2) four blood samples from pregnant women in early pregnancy with lysed mother RBC were collected, kept at 4° C. before processing as a part of stability study, and that fetal/embryonic cells could be separated in a FACS sorter after incubation with a basic pH-sensitive fluorescent dye.

Example 7

This example demonstrated that fetal/embryonic cells in peripheral mother blood could be identified and isolated, exploiting their preferential maintenance of a more basic pH level than their surrounding media or other blood borne cells. In this example, a pH-sensitive fluorescent dye was added to peripheral blood of pregnant women, and the fluorescent signal corresponding to the dye internalized in cells was significantly higher for cells with more basic pH. This signal was then used for detection, counting, and separation in a flow cytometer or sorter machine. In the present example a fluorescence-activated cell sorting (FACS) system was used. Verification that the fraction of cells separated using the method of the present invention did contain fetal cells was performed using the real-time PCR technique Quantifiler® Duo DNA Quantification Kit (Applied Biosystems®) for quantitative and qualitative assessment of total human and human male DNA in a sample.

Since it was expected that about 50% of the samples should contain the male (fetus) DNA (when the number of samples is large enough to become statistically significant), and since all samples should have human DNA, its subsequent identification and quantification in the isolated cell fraction in the FACS machine may be used to demonstrate the utility of the present invention for isolation of fetal cells in maternal blood, and may further be used to calculate the purification factor afforded by the present invention.

3.5 ml of whole blood was collected from three pregnant women, with pregnancy status confirmed by HCG testing and additionally age of gestation by ultrasound, following consent by an Institutional Review Board approved study at a clinical site (Planned Parenthood of Southern New England, New Haven, Conn.). The de-identified samples were arbitrarily marked 019, 020, and 022. Blood was processed within 36 hours of collection and examined by a BD FACSARIA II SORP cell sorting machine, following incubation with a fluorescent dye (BCECF AM). The samples were kept at 4° C. after collection and before processing.

1 mg of BCECF AM (Invitrogen) was dissolved in 1 ml of DMSO and 10 aliquots were prepared. 2 aliquots were dissolved in 10 ml of Hank's balanced salt solution in order to make a working solution (0.016 mM). The working solution of BCECF AM was added to samples (3.5 ml of BCECF AM to 3.5 ml of sample) and incubated at room temperature for 40 minutes. Lysis of the RBCs then was performed, after staining by fluorescent dye (BCECF AM), by adding to the sample 20 ml of RBC lysis buffer (BioLegend) to each sample (2 ml of buffer was dissolved in 20 ml of distillate water and incubated with a blood sample for 10 minutes at room temperature). PBS was then added to result in a total volume of 50 ml, followed by centrifugation (2000 rpm for 10 min) and removal of the supernatant.

2 ml of each sample was introduced for analysis by a cell sorter (BD FACSARIA II SORP) and the data analyzed by the system software. The fetal/embryonic cells were further sorted and isolated in a tube containing 0.1 ml of PBS. The sorted samples subsequently were processed with a real time PCR protocol.

Samples 019 and 022 showed a positive signal for male DNA, while sample 022 was negative. Quantitative analysis of data showed that the ration between fetal and maternal DNA was between 1:400 to 1:700. Quantitative analysis of data also showed, taking in account the total number of sorted cells per sample (50,000), that about 100 fetal cells were recovered from 3.5 ml of maternal blood.

Figure 9A:
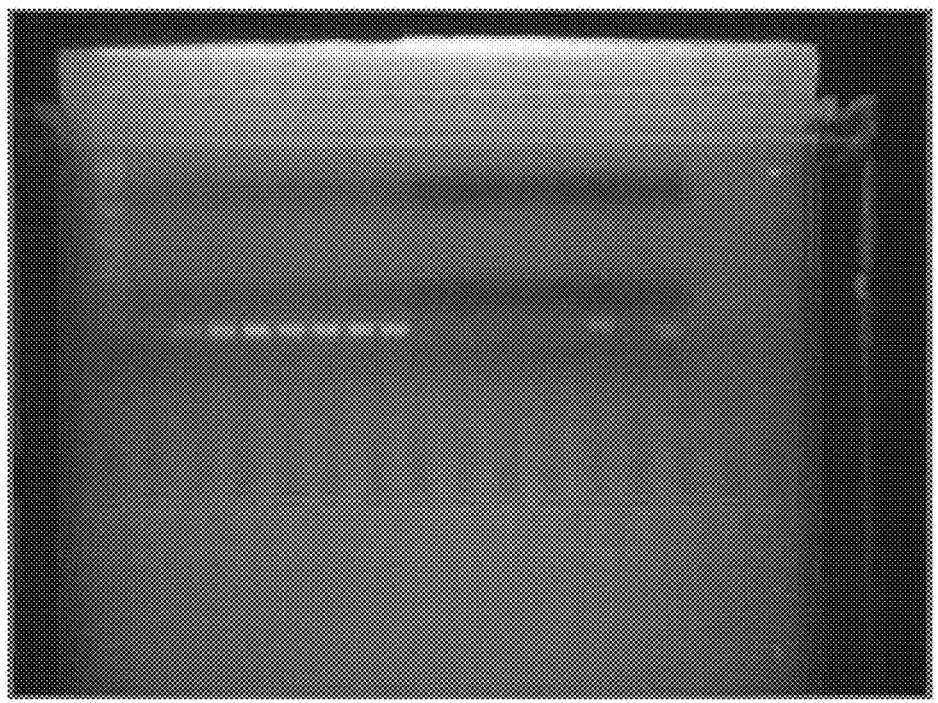
FIGS. 9A-9C illustrate the presence of DNA, in accordance with certain embodiments of the invention.
Figure 9B:
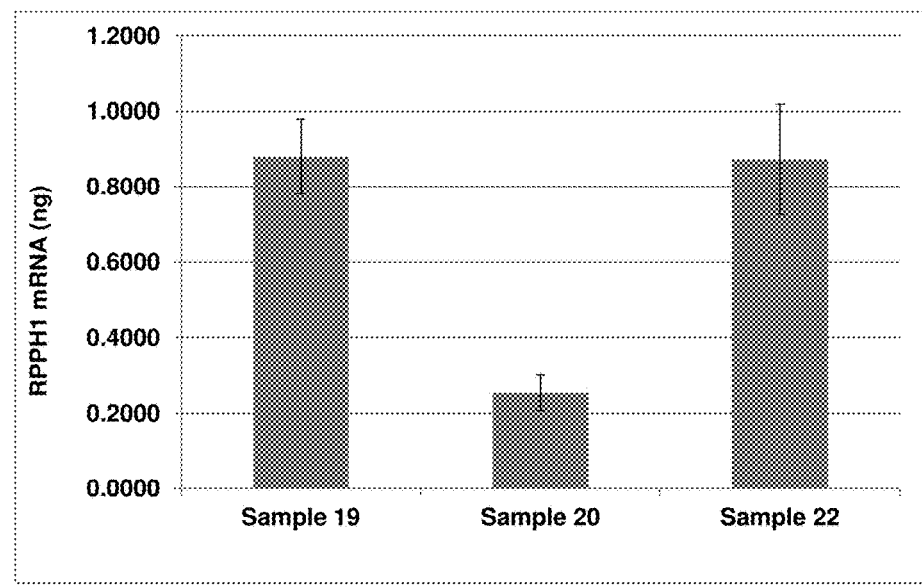
Figure 9C:
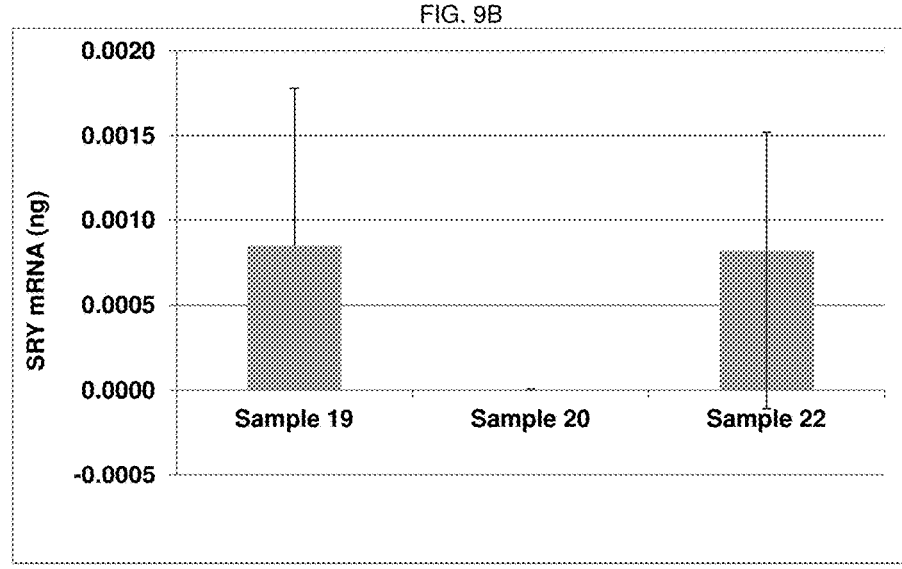

Three blood samples from pregnant women in early pregnancy with lysed mother RBC were collected. The gestation age of the samples was 6 weeks and 4 days for sample 019, 7 weeks and 1 day for sample 020, and 5 weeks and 5 days for sample 022. Fetal/embryonic cells could be separated in a FACS sorter after incubation with a basic pH-sensitive fluorescent dye. A picture of the electrophoresis gel showing presence of male DNA in samples 019 and 022 is shown in FIG. 9A. A graph showing a quantity of human DNA in the samples 019, 020, and 022 is shown in FIG. 9B. A graph showing a quantity of male DNA in the samples 019, 020, and 022 is shown in FIG. 9C.

Example 8

In this example, it was demonstrated that fetal/embryonic cells in peripheral mother blood can be identified and isolated, exploiting their preferential maintenance of a more basic pH level than their surrounding media or other blood borne cells. In this example, a pH sensitive fluorescent dye was added to peripheral blood of pregnant women, and the fluorescent signal corresponding to the dye internalized in cells was significantly higher for cells with more basic pH. This signal was then used for detection, counting, and separation in a flow cytometer or sorter machine, in the present example, using a Fluorescence-Activated Cell Sorting (FACS) system. This example further demonstrated that the natural pH difference between fetal and maternal cells may be sufficiently large to enable a high degree of purification (ratio of fetal to maternal cells in the isolated cell fraction), especially when extra care is taken to avoid other pH modifying agents that may penetrate all cells in the sample. As an example, certain RBC cell lysing agents may contain compounds that can increase intercellular pH and thus reduce the overall difference between fetal and maternal cells. In this example, it is shown that avoiding lysing agents increased the overall purity of the isolated cell fraction. Verification that the fraction of cells that were separated contained fetal cells was performed using real time PCR techniques: Quantifiler® Duo DNA Quantification Kit (Applied Biosystems®) for quantitative and qualitative assessment of total human and human male DNA in a sample.

Since it is expected that about 50% of the samples should contain the male (fetus) DNA (i.e., when the number of samples is large enough to become statistically significant), and since all samples should have human DNA, its subsequent identification and quantification in the isolated cell fraction in the FACS machine may be used to demonstrate the utility of the present invention for isolation of fetal cells in maternal blood, and may further be used to calculate the purification factor.

Figure 10:
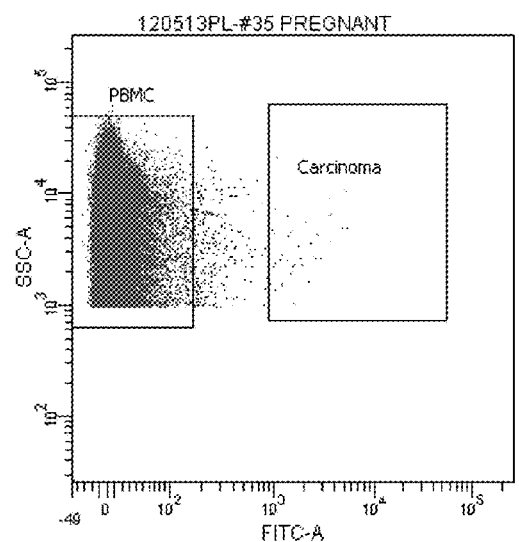
FIG. 10 illustrates purification using non-lysed blood, in accordance with certain embodiments of the invention.

This example demonstrated three blood samples from pregnant women in early pregnancy without lysis of mother RBC. The gestation age of the samples was 7 weeks and 3 days for sample 034 (arbitrary labeled), 5 weeks and 0 day for sample 035, and 9 weeks and 6 days for sample 036. Fetal/embryonic cells could be separated in a FACS sorter after incubation with a basic pH sensitive fluorescent dye (FIG. 10 for sample 035 which was positive also for Y chromosome).

3.5 ml of whole blood was collected from three pregnant women, with pregnancy status confirmed by HCG testing and additionally age of gestation by ultrasound, following consent by an Institutional Review Board approved study at a clinical site (Planned Parenthood of Southern New England, New Haven, Conn.). The de-identified samples were marked 034, 035, 036. Blood was processed within 36 hours of collection and examined by a BD FACSARIA II SORP cell sorting machine, following incubation with a fluorescent dye (BCECF AM). The samples were kept at 4° C. after collection and before processing.

1 mg of BCECF AM (Invitrogen) was dissolved in 1 ml of DMSO and 10 aliquots were prepared. 2 aliquots were dissolved in 10 ml of Hank's Balanced Salt Solution in order to make working concentration (0.016 mM). A working solution of BCECF AM was added to samples (3.5 ml of BCECF AM to 3.5 ml of sample) and incubated in room temperature for 40 minutes. Lysis of RBC was not performed. As mentioned earlier, one component in the RBC lysis buffer (BioLegend) is ammonium chloride, which nonspecifically increases intracellular pH in cells of different origin, including adult neutrophils, possibly causing nonspecific background increase for the assay and thus reducing difference in pH inherent in the untreated sample. PBS was then added to result in a total volume of 50 ml, followed by centrifugation (2000 rpm for 10 min) and removal of the supernatant. 2 ml of each sample was introduced for analysis by a cell sorter (BD FACSARIA II SORP) and data analyzed by the system software. Fetal/embryonic cells were further sorted and isolated in a tube containing 0.2 ml of PBS. The sorted samples underwent real time PCR protocol.

Samples 035 showed positive signal for male DNA, samples 034 and 036 were negative, and the total number of sorted for PCR cells in sample 035 was 50 cells.

Example 9

In this example, it was demonstrated that fetal/embryonic cells in peripheral mother blood can be identified and isolated, exploiting their preferential maintenance of a more basic pH level than their surrounding media or other blood borne cells. In this example, intracellular pH sensitive fluorescent dye was added to peripheral blood of pregnant women, and the fluorescent signal corresponding to the dye internalized in cells was found to be significantly higher for cells with more basic pH. This signal was then used for detection, counting, and separation in a flow cytometer or sorter machine; in the present example, this was a Fluorescence-Activated Cell Sorting (FACS) system. Verification that the fraction of separated cells did contain fetal cells was performed using DNA FISH (AneuVysion Multicolor DNA probe Kit, Abbott) for Y and X chromosomes. Specifically, while X chromosomes are found in both the maternal and fetal cells, it was expected that Y chromosomes would be found in about one-half of the total number of samples detected, since it could not have been originated from maternal origin.

The gestation age of the samples was 6 weeks and 3 days for sample 033, 5 weeks and 0 day for sample 035 (arbitrary labeled). 3.5 ml of whole blood was collected from three pregnant women, with pregnancy status confirmed by HCG testing and additionally age of gestation evaluation by ultrasound, following consent by an Institutional Review Board approved study at a clinical site (Planned Parenthood of Southern New England, New Haven, Conn.). The de-identified samples were marked 033, 035. Blood was processed within 36 hours of collection and examined by a BD FACSARIA II SORP cell sorting machine, following incubation with a fluorescent dye (BCECF AM). The samples were kept at 4° C. after collection and before processing.

1 mg of BCECF AM (Invitrogen) was dissolved in 1 ml of DMSO and 10 aliquots were prepared. 2 aliquots were dissolved in 10 ml of Hank's Balanced Salt Solution in order to make working concentration (0.016 mM). A working solution of BCECF AM was added to samples (3 ml of BCECF AM to 3.5 ml of sample) and incubated in room temperature for 40 minutes. Lysis of the RBCs was then performed for sample 033. After staining by fluorescent dye (BCECF AM) by adding to the sample 20 ml of RBC lysis buffer (BioLegend), 2 ml of buffer was dissolved in 20 ml of distillate water and incubated with a blood sample for 10 minutes in room temperature. PBS was then added up to 50 ml total volume, followed by centrifugation (1600 rpm for 10 min) and removal of the supernatant. Lysis of RBC was not performed for sample 035. After staining by fluorescent dye (BCECF AM) PBS was added up to 50 ml total volume, followed by centrifugation (1600 rpm for 10 min) and removal of the supernatant.

2 ml of each sample was introduced for analysis by a cell sorter (BD FACSARIA II SORP) and the data analyzed by the system software. Fetal/embryonic cells were further sorted and isolated on poly-L-lysine microscopic glass slides, and after air drying for 15 minutes, the slides were fixed in 4% paraformaldehyde for 20 minutes. The slides were the washed in PBS three times, 5 minutes for each of the washing step. The slides underwent DNA FISH staining (AneuVysion Multicolor DNA probe Kit, Abbott) for Y and X chromosomes. On the slide 033, 11 cells were present for analysis after FISH staining, and 7 cells were shown to be positive for Y chromosome (63.6% purity level). On the slide 035, 7 cells were present for FISH analysis and 5 cells were positive for Y chromosome (71.4% purity).

Figures 11A, 11B:
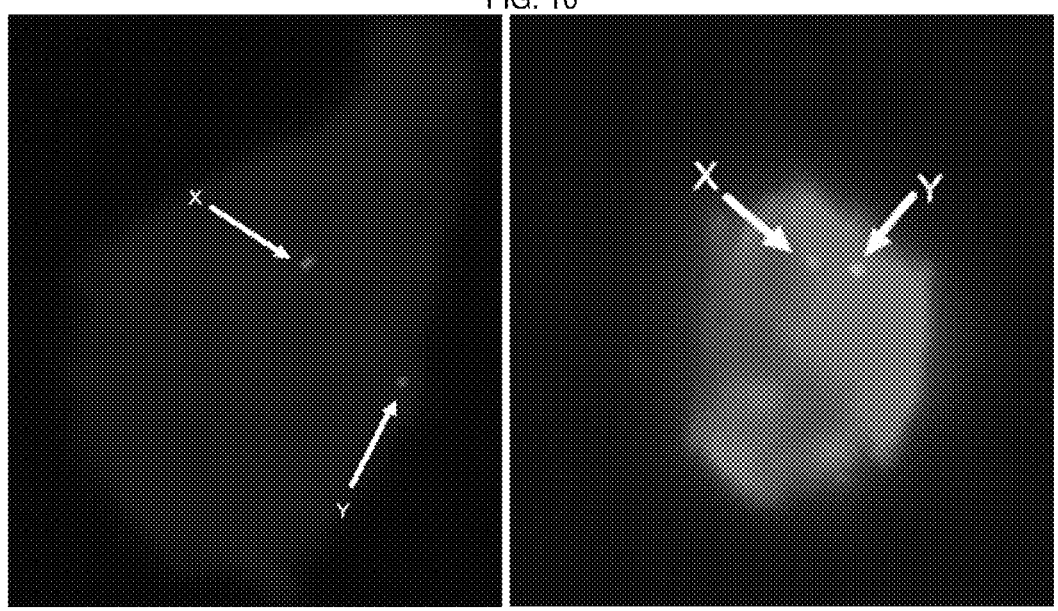
FIG. 11A-11B illustrate the presence of Y chromosome in fetal cells, in accordance with certain embodiments of the invention.

This example demonstrates that Y chromosome positive cells by DNA FISH (presumably from a male fetus) could be separated by a FACS sorter after incubation with an intracellular pH sensitive fluorescent dye with high purity from blood samples of pregnant women in early pregnancy with and without lysis of maternal RBC (FIGS. 11A and 11B).

Example 10

In this example, it was demonstrated that human cancer cells in peripheral blood could be identified and isolated exploiting their preferential maintenance of a more basic pH and cell granularity or internal complexity level than their surrounding media or other blood borne cells. In this example, intracellular pH sensitive fluorescent dye was added to carcinoma cells and normal blood cells, and the fluorescent signal corresponding to the dye internalized in cells with more basic intracellular pH is used for detection, counting, and potential separation in a flow cytometer or sorter machine; in the present examples, using a Fluorescence-Activated Cell Sorting (FACS) system. The sorted cells were presented in a well-preserved state, which allowed following cytopathological and genetic analyses.

CRL-2422 cells (human prostate adenocarcinoma) were obtained from ATCC and 2 ml of whole blood was collected from non-pregnant women without any history of cancer following consent by an Institutional Review Board approved study at a clinical site (Planned Parenthood of Southern New England, New Haven, Conn.). The de-identified sample was marked 4a001 (arbitrary labeled). Blood was processed within 36 hours of collection. The sample was kept at 4° C. after collection and before processing. 2 ml of blood was mixed with approximately 10,000 of prostate carcinoma cells (CRL-2422) and incubated with BCECF AM.

1 mg of BCECF AM (Invitrogen) was dissolved in 1 ml of DMSO and 10 aliquots were prepared. One aliquot was dissolved in 10 ml of Hank's Balanced Salt Solution in order to prepare working concentration (0.016 mM). The working solution of BCECF AM was then added to samples (2 ml of BCECF AM to 2 ml of sample) and incubated in room temperature for 40 minutes. Lysis of RBC was performed after staining by fluorescent dye (BCECF AM) by addition of 15 ml of distillate water to the sample for 30 seconds. PBS was then added up to 50 ml total volume, followed by centrifugation (1500 rpm for 10 min) and removal of the supernatant. The sample was introduced for analysis by BD FACSARIA II SORP machine and the data analyzed by the system software. CRL-2422 cells were further sorted and isolated on a glass slide.

Figure 12A:
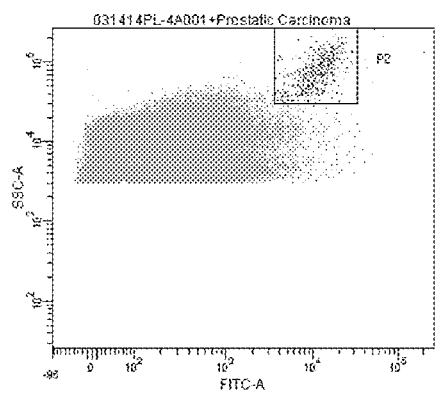
FIGS. 12A-C illustrates determination of carcinoma cells, in accordance with certain embodiments of the invention.
Figure 12B:
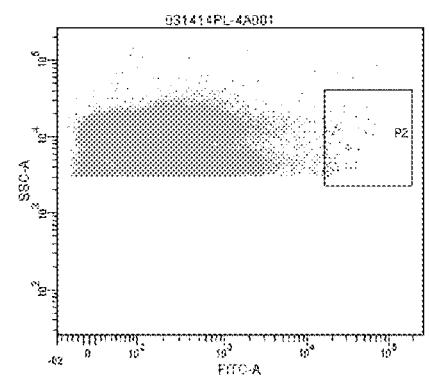

This example demonstrates that carcinoma cells were distinguished by strong fluorescent signal and higher cell granularity/internal complexity when incubated with a intracellular pH sensitive fluorescent dye than normal blood cells in the mixed sample (FIG. 12A), while normal circulating blood cells were not distinguished by strong fluorescent signal and high cells granularity/internal complexity after being incubated with same dye (FIG. 12B). In addition, cells sorted from population of strong fluorescent signal and high cell granularity/internal complexity from a sample of mixed normal blood and carcinoma cells and stained by H&E stain exhibited characteristic morphology corresponding to carcinoma cells (FIG. 12C).

FIGS. 12A-B illustrate the presence of strong fluorescent signal and higher cell granularity/internal complexity for carcinoma cells when incubated with an intracellular pH sensitive fluorescent dye, than for normal blood cells in a mixed sample.

Figure 12C:
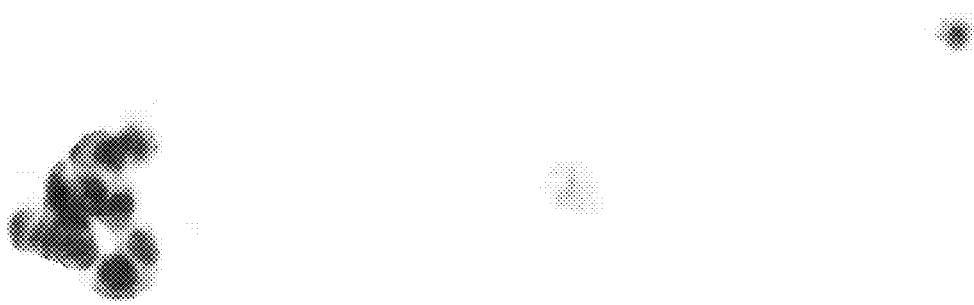

FIG. 12C illustrate cells with morphological features corresponding to carcinoma cells, which were selected from a population of cells with strong fluorescent signal and high cell granularity/internal complexity in a general mixture of normal blood and carcinoma cells stained by H&E.

Example 11

In this example, it was demonstrated that fetal/embryonic cells that were identified originate from the fetus and not from fetal cells that might persistent from prior pregnancies. In this example, fetal/embryonic cells were determined from the maternal blood of women who were confirmed as not pregnant at the time of collection of blood sample, but with history of pregnancy with a male fetus. In this example, intracellular pH sensitive fluorescent dye was added to peripheral blood of non-pregnant women with a history of previous male pregnancy, and the fluorescent signal corresponding to the dye internalized in cells is some of the cells was higher reflecting more basic intracellular pH. This signal was then used for attempt for detection, counting, and separation of cells using a Fluorescence-Activated Cell Sorting (FACS) system from the blood of non-pregnant women with previous male pregnancy. Verification that the fraction of cells separated did not contain fetal cells was performed using real time PCR for Y chromosome.

3.5 ml of whole blood was collected from six non-pregnant women with history of at least one prior male pregnancy (and at least 6 months before sample collection), with current non-pregnancy status confirmed by HCG testing, following consent by an Institutional Review Board approved study at a clinical site (Planned Parenthood of Southern New England, New Haven, Conn.). Blood was processed within 36 hours of collection and examined by a BD FACSARIA II SORP cell sorting machine, following incubation with a fluorescent dye (BCECF AM). The samples were kept in 4° C. after collection and before processing.

1 mg of BCECF AM (Invitrogen) was dissolved in 1 ml of DMSO and 10 aliquots were prepared. 2 aliquots were dissolved in 10 ml of Hank's Balanced Salt Solution in order to make working concentration (0.016 mM). A working solution of BCECF AM was added to the samples (3 ml of BCECF AM to 3.5 ml of sample) and incubated at room temperature for 40 min. Lysis of RBC then was performed, after staining by fluorescent dye (BCECF AM) by adding to the sample 15 ml of distillate water for 30 seconds. PBS was then added up to 50 ml total volume, followed by centrifugation (1500 rpm for 10 min) and removal of the supernatant. The sample was introduced for analysis by BD FACSARIA II SORP machine and the data analyzed by the system software. 100,000 events were recorded, with the sorting gate for subsequent collection set to include only most high fluorescence cells (30-50 cells per 100,000 events). 400 cells were sorted in the tubes with PBS for real time PCR.

Figure 13A:
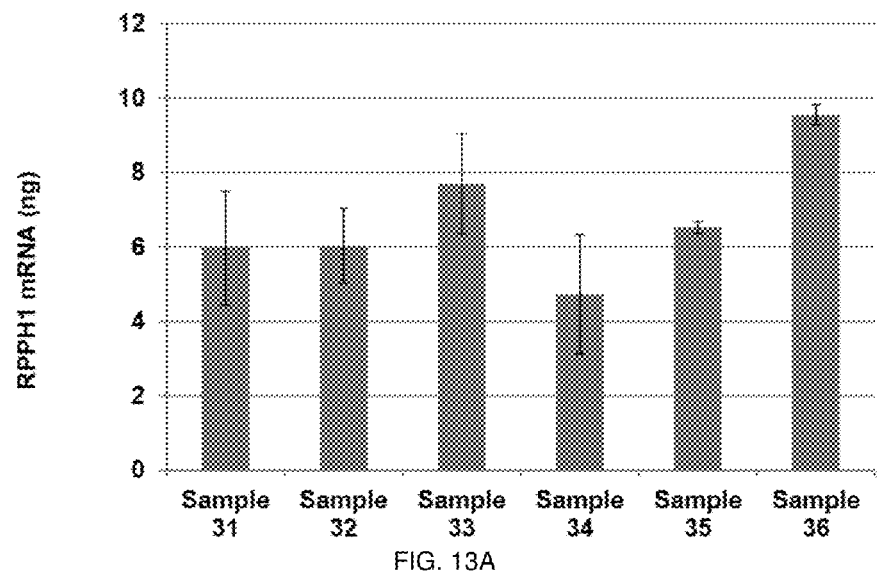
FIGS. 13A-13C illustrate mRNA isolated from cells isolated from blood obtained from non-pregnant women with prior male pregnancies, in accordance with certain embodiments of the present invention.
Figure 13B:
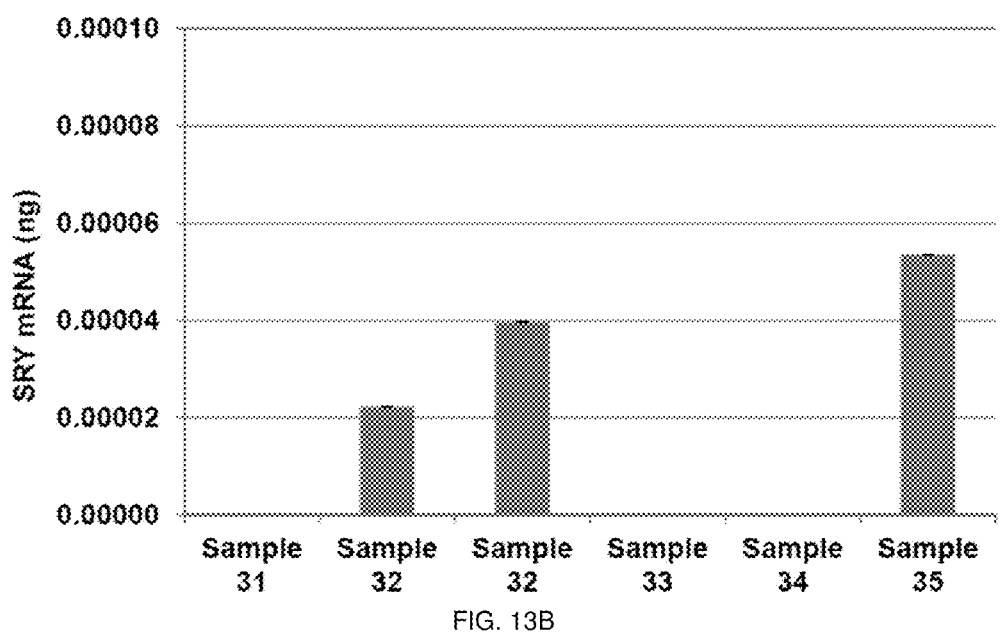
Figure 13C:
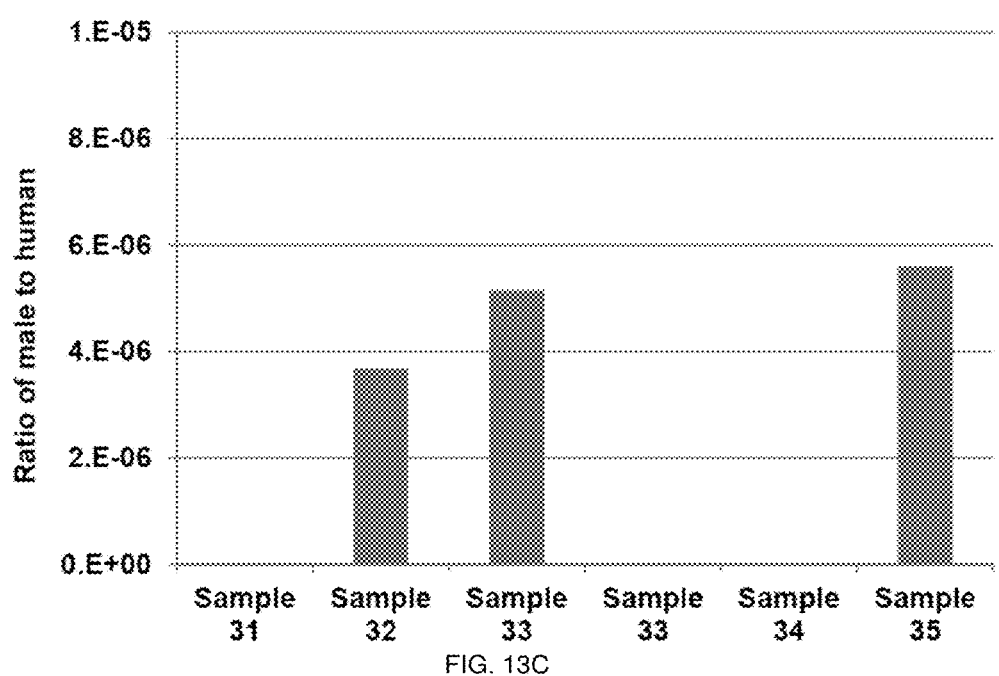

This example specifically demonstrates human mRNA (ng) for the six tested samples (FIG. 13A), with male mRNA (ng) for six tested samples being below an acceptable minimum level of detection of mRNA in the PCR experiments (FIG. 13B). FIG. 13C shows the ratio of male to human mRNA.

FIG. 13A illustrates an amount of human mRNA in cells isolated from blood obtained from non-pregnant women with a prior male pregnancy. FIG. 13B illustrates an amount of male mRNA in cells isolated from blood obtained from non-pregnant women with a prior male pregnancy. FIG. 13C illustrates the ratio of male to total mRNA in cells isolated from blood obtained from non-pregnant women with a prior male pregnancy.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. In addition, as used herein the term "about" refers to +/−10%. In addition, when the word "about" is used herein in reference to a number, it should be understood that still another embodiment of the invention includes that number not modified by the presence of the word "about."

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of determining circulating cancer cells within blood from a subject suspected of having cancer, the method comprising:
    exposing a blood sample arising from a subject suspected of having cancer to a solution comprising a pH-sensitive entity, wherein the blood sample is suspected of containing circulating cancerous cells and non-cancerous cells, and wherein the pH-sensitive entity consists of a pH sensitive dye or a plurality of pH sensitive dyes and is more fluorescent or less fluorescent within the cancer cells relative to non-cancerous cells;
    determining the pH-sensitive entity internally within at least some of the cells within the blood sample by determining fluorescence of the cells;
    isolating suspected circulating cancerous cells based on the determination of the fluorescence of the cells; and
    confirming that at least some of the isolated cells are cancer cells.

2. The method of claim 1, further comprising acidifying the blood sample prior to determining the pH-sensitive entity internally within at least some of the cells within the blood sample.

3. The method of claim 2, wherein acidifying the blood sample comprises introducing an acid to the blood sample.

4. The method of claim 3, wherein the acid comprises ethylenediaminetetraacetic acid.

5. The method of claim 2, wherein acidifying the blood sample comprises containing the blood sample in an airtight container.

6. The method of claim 1, wherein the pH-sensitive entity comprises one or more of 2',7'-bis(2-carboxyethyl)-5(6)-carboxyfluorescein tetrakis(acetoxymethyl) ester (BCECF AM), 5(6)-carboxy-2',7'-dichlorofluorescein, 5(6)-carboxyfluorescein, 5(6)-carboxyfluorescein diacetate, 5(6)-carboxyfluorescein N-hydroxysuccinimide ester, 3,6-diacetoxyphthalonitrile, 6,8-dihydroxy-1,3-pyrenedisulfonic acid disodium salt, Eosin diacetate, or naphthofluorescein.

7. The method of claim 1, comprising determining the fluorescence of the cells using a flow cytometer.

8. The method of claim 1, comprising determining fluorescence of the cells using a fluorescence microscope.

9. The method of claim 1, comprising performing a genetic analysis on at least some of the isolated cells.

10. The method of claim 9, wherein the genetic analysis is used to determine genetic abnormalities within at least some of the isolated cells.

11. The method of claim 9, wherein the genetic analysis is used to confirm at least some of the isolated cells are cancer cells.

12. The method of claim 1, comprising sequencing DNA from at least some of the isolated cells.

13. The method of claim 1, comprising performing PCR on at least some of the isolated cells.

14. The method of claim 1, comprising performing FISH analysis on at least some of the isolated cells.

15. The method of claim 1, wherein the subject is not pregnant.

* * * * *